(12) United States Patent
Shinkawa et al.

(10) Patent No.: US 7,064,191 B2
(45) Date of Patent: Jun. 20, 2006

(54) PROCESS FOR PURIFYING ANTIBODY

(75) Inventors: Toyohide Shinkawa, Machida (JP); Kazuhisa Uchida, Machida (JP); Motoo Yamasaki, Machida (JP); Emi Hosaka, Machida (JP); Kenya Shitara, Machida (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 394 days.

(21) Appl. No.: 09/970,154

(22) Filed: Oct. 4, 2001

(65) Prior Publication Data

US 2002/0164328 A1    Nov. 7, 2002

Related U.S. Application Data

(60) Provisional application No. 60/268,926, filed on Feb. 16, 2001.

(30) Foreign Application Priority Data

Oct. 6, 2000    (JP)    ................. P. 2000-308254

(51) Int. Cl.
*C07K 1/22*    (2006.01)
*C07K 16/00*    (2006.01)
*G01N 33/53*    (2006.01)

(52) U.S. Cl. ............... 530/413; 424/130.1; 424/137.1; 424/138.1; 424/174.1; 436/547; 436/824; 436/827; 530/387.1; 530/387.5

(58) Field of Classification Search ............ 424/130.1, 424/137.1, 138.1, 174.1; 530/387.1, 387.5, 530/387.7, 413, 415; 436/547, 824, 827
See application file for complete search history.

(56) References Cited

U.S. PATENT DOCUMENTS 5,429,746 A * 7/1995 Shadle et al. ............... 210/635
5,445,332 A * 8/1995 Shimizu et al. ............. 241/100
6,018,032 A   1/2000 Koike et al.
6,342,220 B1 * 1/2002 Adams et al. ............ 424/153.1

FOREIGN PATENT DOCUMENTS

WO    WO 96/33208    10/1996
WO    WO 96/34015    10/1996
WO    WO 98/58964    12/1998
WO    WO 99/10494    3/1999
WO    WO 99/54342    10/1999

OTHER PUBLICATIONS

Boyle et al, Jour. Immunological Methods, 32, 51-58, 1980.*
Bridonneau et al, Jour, Chromatography, 616, 197-204, 1993.*
Danielsson et al, Journal of Immunological Methods, 115, 79-88, 1988.*
Goheen et al, Journal of Chromatography, 326, 235-241, 1985.*
Wright et al, Trends in Biotechnology, Jan. 1997, vol. 15, No. 1, pp. 26-32.
Yamashita et al, The Journal of Biological Chemistry, Apr. 25, 1985, vol. 260, No. 8, pp. 4688-4693.
Shinkawa et al, The Journal of Biological Chemistry, Jan. 31, 2003, vol. 278, No. 5, pp. 3466-3473.
Nose, M. et al., Inhibition of processing of asparagine-linked carbohydrate chains on lgG2a by using swainsonine has no influence upon antibody effector functions in vitro, Journal of Immunology, 1990, vol. 145, No. 3, pp. 910-914.
Dobre, M. A. et al., Isolation of a rabbit lgG fraction with cytophilic properties, Journal of Immunology Methods, 1983, vol. 59, No. 3, pp. 339-348.
Peng, Z. et al., Binding of dog immunoglobulins G.A.M, and E to concanavalin A, Veterinary Immunology Immunopathology, 1993, vol. 36, No. 1, pp. 83-88.
Hiki, Y. et al., Underglycosylation of IgA1 hinge plays a certain role for its glomerular deposition in IgA nephropathy, J. Am. Soc. Nephrol. 1999, vol. 10, No. 4, pp. 760-769.
Kim, H. et al. O-glycosylation in hinge region of mouse immunoglobulin G2b, Journal of Biological Chemistry, 1994, vol. 269, No. 16, pp. 12345-12350.
Abe et al, Journal of Biochemical and Biophysical Methods (1993), vol. 27, pp. 215-227.

* cited by examiner

*Primary Examiner*—David Saunders
(74) *Attorney, Agent, or Firm*—Nixon & Vanderhye P.C.

(57) ABSTRACT

The present invention relates to a process for purifying an antibody having a desired property, which comprises using a substance having an affinity to a carbohydrate binding to the antibody; a medicament comprising, as an active ingredient, the antibody purified by the process; and a method for diagnosing or preventing various diseases, which comprises using a substance having an affinity to a carbohydrate binding to an antibody.

8 Claims, 11 Drawing Sheets

PROCESS FOR PURIFYING ANTIBODY

The present application claims benefit of U.S. Provisional Application Ser. No. 60/268,926, filed Feb. 16, 2001.

BACKGROUND OF THE INVENTION

1. Field of the Invention

The present invention relates to a process for purifying an antibody composition having a desired property. Moreover, it relates to a medicament comprising the antibody composition obtained by the purifying method of the present invention as an active ingredient, and a method for treating various diseases using the antibody composition obtained by a substance having an affinity to the carbohydrate binding to the antibody.

2. Brief Description of the Background Art

Among glycopeptides, the glycopeptides whose carbohydrate structures coordinate toward surface of the proteins can be purified by means of a column to which a lectin binding to a carbohydrate is immobilized. A lectin has a property of specifically binding to a specific carbohydrate structure. Examples of the lectin include a wheat germ lectin, a lentil lectin and the like.

Upon the investigation of binding activity between a wheat germ lectin and a carbohydrate or glycopeptide, among N-glycans, a wheat germ lectin is suggested to have a high binding activity to a hybrid type carbohydrate or a carbohydrate or glycopeptide having sialic acid (*Biochemistry*, 16, 4426 (1977); *The Journal of Biological Chemistry*, 254, 4000 (1979)). Moreover, a wheat germ lectin is suggested to have stronger binding activity to glycopeptides having a carbohydrate structure having bisecting N-acetylglucosamine (*Biochemistry*, 20, 5894 (1981)).

A lentil lectin (hereinafter also referred to as "LCA") is known to recognize monosaccharides, α-D-mannose and α-D-glucose (*The Journal of Biological Chemistry*, 268, 7668 (1993)). It is also known that LCA exhibits a strong binding activity to glycopeptides having a carbohydrate structure wherein L-fucose binds to an N-acetylglucosamine residue which is closest bound to the asparagine residue of N-glycan through α1,6-bond (*Carbohydrate Research*, 40, 111 (1975); *Carbohydrate Research*, 110, 283 (1982)).

However, these facts only indicate that lectins bind to carbohydrates or peptides containing a carbohydrate structure.

An antibody has a carbohydrate which binds to its Fc region (a region after the hinge region of the heavy chain of an antibody), and the carbohydrate is present in a form of being buried in the Fc region, i.e., in a form that the carbohydrate structure is structurally directed to inside of the antibody (*Nature*, 264, 415–420 (1976)).

Nose et al. have employed a column wherein LCA is immobilized to Sepharose carriers, but failed to separate mouse IgG2a. As a result, they considered that it is because the carbohydrate of usual mouse IgG2a produced by a hybridoma cell (12-6 cell) is buried in the Fc region. Also, they have cultured the hybridoma 12-6 cell after the addition of swainesonine which is an agent for inhibiting maturation of an N-glycan to produce IgG2a-class monoclonal antibody and passed the culture product through an LCA-immobilized Sepharose column, thereby the binding of the monoclonal antibody to the column being achieved. However, this is considered to be attributed to the exposure of the sugar chain out of Fc region of the antibody as a result of the conversion of the carbohydrate present in the Fc region of the mouse IgG2a from complex type to hybrid type by the effect of swainesonine (*The Journal of immunology*, 145, 910–914 (1990)).

As described above, the method for purifying an antibody by changing a carbohydrate structure artificially is known but the method for purifying an antibody in consideration of the carbohydrate structure without changing the carbohydrate structure is hitherto unknown.

By the way, the carbohydrate structure present in the Fc region of an antibody is involved in activities of antibody, specifically, antibody-dependent cell-mediated cytotoxic activity (hereinafter also referred to as "ADCC activity"), complement-dependent cytotoxic activity (hereinafter also referred to as "CDC activity"), in vivo stability, and the like.

It is known that the addition of galactose residue to a non-reducing end of a carbohydrate structure increases CDC activity of an antibody (*Molecular Immunol.*, 32, 1311 (1995); WO98/58964), the increase of the content of bisecting N-acetylglucosamine-bound carbohydrate in Fc region of an antibody increases ADCC activity of the antibody (WO99/54342), and the increase of the content of sialic acid enhances in vivo stability (*Nature Biotechnology*, 17, 1116 (1999)). However, a process for purifying an antibody having a desired property such as effector activities including ADCC activity and CDC activity, or in vivo stability, while attention being paid to the carbohydrate structure relating to these activities is unknown hereto.

Also, in rheumatism, an autoimmune disease, the amount of galactose of IgG in patient's blood is known to decrease (*Glycoconjugate Journal*, 15, 929–934 (1998)). As a conventional diagnosis, a lectin blot method by a lectin is employed but the method requires complex operations including a step of modifying an antibody in a living body.

SUMMARY OF THE INVENTION

An object of the present invention is to obtain an antibody composition having a desired property in a high purity by purifying the antibody composition depending on the difference of the carbohydrate structure which binds to the Fc region. Moreover, it is expected to employ an antibody composition in a living body purified by said process for diagnosing various diseases. Furthermore, an antibody composition having a desired property can be purified from an antibody produced in an animal cell or the like. Especially, the antibody composition having a high ADCC activity which is purified by the process of the present invention is expected to be capable of activating immune system in a living body and thus is expected to have usefulness for treating various human diseases including an antitumor effect.

The present invention relates to the following (1) to (21).

(1) A process for purifying an antibody composition having a desired property, which comprises using a substance having an affinity to a carbohydrate binding to the antibody.

(2) The process according to (1), wherein the carbohydrate is an N-glycan.

(3) The process according to (2), wherein the N-glycan is a carbohydrate to which bisecting N-acetylglucosamine, fucose or galactose is bound.

(4) The process according to (1), wherein the substance having an affinity to a carbohydrate is a lectin.

(5) The process according to (4), wherein the lectin is at least one lectin selected from the group consisting of a concanavalin A, a wheat germ lectin, a lentil lectin and a *Phaseolus vulgaris* lectin $E_4$.

(6) The process according to (1), wherein the substance having an affinity to the carbohydrate is bound to a carrier.

(7) The process according to (6), wherein the carrier is a synthetic resin polymer.

(8) A process for purifying an antibody composition comprising an antibody having a carbohydrate structure to which bisecting N-acetylglucosamine is bound, which comprises using a column to which a wheat germ lectin or a *Phaseolus vulgaris* lectin $E_4$ is immobilized.

(9) A process for purifying an antibody composition having a high antibody-dependent cell-mediated cytotoxic activity, which comprises using a column to which a wheat germ lectin or a *Phaseolus vulgaris* lectin $E_4$ is immobilized.

(10) A process for purifying an antibody composition comprising an antibody having a carbohydrate structure to which fucose is bound, which comprises using a column to which a *Lens culinaris* lectin is immobilized.

(11) A process for purifying an antibody composition having a high antibody-dependent cell-mediated cytotoxic activity, which comprises using a column to which a *Lens culinaris* lectin is immobilized.

(12) A process for purifying an antibody composition comprising an antibody having a carbohydrate structure to which galactose is bound, which comprises using a carrier for hydrophobic chromatography.

(13) A process for purifying an antibody composition having a high complement-dependent cytotoxic activity or antibody-dependent cell-mediated cytotoxic activity, which comprises using a carrier for hydrophobic chromatography.

(14) The process according to (13), wherein a phenyl group is bound to the carrier for hydrophobic chromatography.

(15) A process for purifying an antibody composition having a desired property, which comprises combining the process according to any one of (1) to (14).

(16) The process according to any one of (1) to (15), wherein the antibody is human IgG.

(17) The process according to (16), wherein the subclass of the human IgG is IgG1.

(18) A medicament comprising, as an active ingredient, the antibody composition purified by the process according to any one of (1) to (17).

(19) The medicament according to (18), wherein the antibody is human IgG.

(20) The medicament according to (19), wherein the subclass of the human IgG is IgG1.

(21) A method for diagnosing various diseases, which comprises using a substance having an affinity to a carbohydrate binding to an antibody.

DETAILED DESCRIPTION OF THE INVENTION

Figure 1:
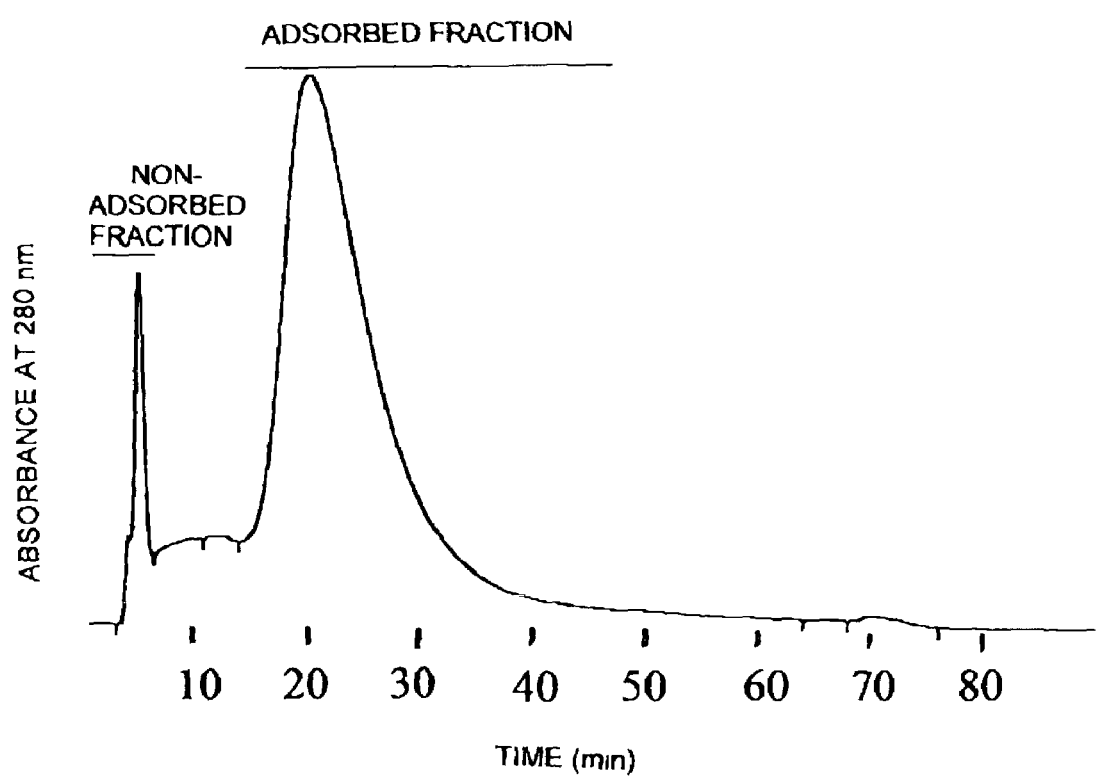
FIG. 1 is a drawing showing elution of separating an anti-hIL-5Rα CDR-grafted antibody composition using a column to which a lectin binding to a carbohydrate having fucose is immobilized. The ordinate and the abscissa indicate the absorbance at 280 nm of UV and the elution time, respectively.

In the present invention, a high complement-dependent cytotoxic activity or antibody-dependent cell-mediated cytotoxic activity of an antibody composition means that the antibody composition after purification has a higher CDC activity or ADCC activity than the antibody composition before passing through a column.

An antibody is a glycopeptide produced in vivo by immunoreaction as a result of stimulation with an extraneous antigen, and has an activity of specifically binding to the antigen.

The antibody purified in the present invention may be any antibody including an antiserum obtained immunizing an animal with an antigen, a monoclonal antibody secreted by a hybridoma cell prepared from a spleen cell of an animal immunized with an antigen, an antibody which is genetically produced, i.e., an antibody obtained by inserting an antibody gene into an antibody expression vector and introducing the vector into a host cell. Furthermore, the antibody of the present invention includes a fused protein with which Fc region of an antibody is fused and the like.

Examples include a mouse antibody obtained from a spleen cell after immunization of mouse, a human chimeric antibody and a human complementarity determining region (hereinafter referred to as "CDR")-grafted antibody (*Nature*, 321, 522 (1986)) produced by using a host cell into which genes of a mouse antibody and a human antibody are optionally incorporated (*Proc. Natl. Acad. Sci., U.S.A.*, 81, 6851 (1984)), and the like.

As an antibody, human IgG (immunoglobulin) is preferable, and human IgG belonging to a subclass of IgG1 is more preferable.

The Fc region of an antibody has a region to which N-glycan is bound at one position per each heavy chain, and therefore, two carbohydrates are bound to one molecule of the antibody. Since the N-glycan which is bound to an antibody includes any carbohydrate represented by Compound (I), there exist a number of combinations of carbohydrates as the two N-glycans. Therefore, the antibody is the same as the known purified antibody from a viewpoint of the amino acid sequence, but is regarded as an antibody composition because various carbohydrates exist in the carbohydrate structure bound to the Fc region of the purified antibody.

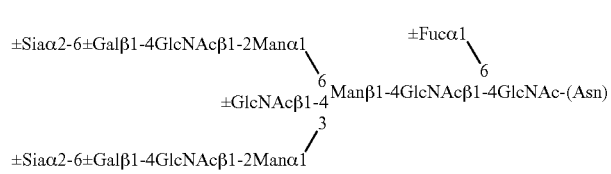

(I)

Any carbohydrate may be used, so long as it is a linear or branched oligosaccharide or polysaccharide. The carbohydrate is roughly classified into N-glycans which are bound to asparagine and O-glycans which are bound to serine, threonine or the like. The N-glycans include a high-mannose-type, a complex-type and a hybrid-type.

An oligosaccharide is a compound obtained by dehydratively binding 2 to 10 monosaccharides or substituted derivatives of monosaccharides. A saccharide formed by binding a larger number of monosaccharides is called a polysaccharide. Different kinds of polysaccharides exist depending on the constituting saccharides. A saccharide containing a large amount of uronic acid or ester-sulfuric acid is called an acidic polysaccharide, and a polysaccharide containing only neutral saccharides is called a neutral polysaccharide. Among the polysaccharides, a group of polysaccharides called mucopolysaccharides are mostly bound to a protein, and are called proteoglycan.

A monosaccharide is a constituting unit of a carbohydrate, and is an elemental substance which will not be hydrolyzed to a molecule simpler than itself. A monosaccharide is roughly classified into three kinds: an acidic sugar having an acidic side chain such as a carboxyl group or the like; an aminosugar in which a hydroxyl group is substituted with an amino group; and a neutral sugar other than the above two groups. As the monosaccharides present in the living body, the acidic sugar includes sialic acid such as N-acetyl-neuraminic acid and N-glycolylneuraminic acid (hereinafter referred to as "Neu5Gc"), etc., uronic acid and the like; the aminosugar includes N-acetylglucosamine (hereinafter referred to as "GlcNAc"), N-acetylgalactosamine and the like; and the neutral sugar includes glucose, mannose, galactose, fucose and the like.

The carbohydrate which is bound to an antibody includes the three types of N-glycans.

The N-glycan has an elemental common core structure as shown below.

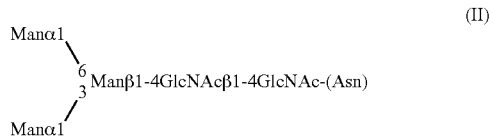

(II)

In the above structure, the terminal to be bound to asparagine is referred to as reducing terminal and the opposite side is referred to as non-reducing terminal.

As the substance having an affinity to a carbohydrate, any substance having a property of binding to a carbohydrate can be used. Examples includes a protein, an antibody, a low molecular weight compound and the like.

The protein having an affinity to a carbohydrate includes a sugar-binding protein such as a mannose-binding protein, a fibroblast growth factor, an epidermal growth factor, etc., a lectin, a lectin-like substance and the like.

A lectin is a generic term of proteins having an affinity to a saccharide present in all living organisms such as animals, plants, microorganisms and the like. The lectin is defined by the following (1) to (3).

(1) It binds to a saccharide and aggregates cells or precipitates glycoconjugates.

(2) It is a non-immunological product.

(3) Its binding to a cell or a glycoconjugate is blocked by a monosaccharide or an oligosaccharide.

A glycoconjugate is a generic term of biomolecules including saccharides and includes glycopeptide, proteoglycan and glycolipid.

Examples of the lectin include concanavalin A (hereinafter referred to as "ConA") derived from sword beans (English name: Jack bean; botanical name: *Conavalia ensiformis*), a wheat germ lectin (hereinafter referred to as "WGA") derived from wheat germ (botanical name: *Triticum vulgaris*), a LCA derived from lentils (botanical name: *Lens culinaris*), a *Phaseolus vulgaris* lectin $E_4$ (hereinafter referred to as "PHA-$E_4$") derived from snap beans (botanical name: *Phaseolus vulgaris*), a *Ricinus communis* lectin (hereinafter referred to as "RCA") derived from caster beans (botanical name: *Ricinus communis*) and the like.

ConA recognizes α-D-mannose and α-D-glucose. Since ConA strongly binds to an N-glycan, it is a lectin most widely used.

WGA has a high binding ability to a hybrid-type carbohydrate and a glycopeptide having sialic acid, and its binding is strengthened when bisecting GlcNAc is present.

Bisecting GlcNAc is GlcNAc which is bound to a mannose residue via a β1,4-bond in the above formula (I).

LCA recognizes α-D-mannose and α-D-glucose. It shows a strong binding ability to a structure in which L-fucose binds to a GlcNAc residue which is closest bound to asparagine of an N-glycan via an α1,6-bond.

PHA-$E_4$ binds to a double-stranded or triple-stranded asparagine-bound carbohydrate, and its binding is strengthened when bisecting GlcNAc is present.

RCA recognizes β-D-galactose and binds to an O-glycan and/or an N-glycan having β-galactose at a non-reducing end. Especially, it has a strong affinity to a complex-type carbohydrate having a galactoseβ1-4GlcNAc structure.

The antibody having an affinity to a carbohydrate includes a monoclonal antibody against a carbohydrate secreted by a hybridoma cell prepared from a spleen cell of an animal immunized with a carbohydrate, a recombinant antibody having an affinity to a carbohydrate obtained by isolating an antibody gene from the monoclonal antibody, inserting the antibody gene into an antibody-expressing vector and introducing the vector into a host cell to produce the antibody in the host cell.

Examples of the antibody include a mouse antibody obtained from a spleen cell of an immunized mouse; a human chimeric antibody or a human CDR-grafted antibody produced by using a host cell into which genes of a mouse antibody and a human antibody are optionally incorporated; the antibody fragments thereof such as Fab, Fab', F(ab)$_2$, a single stranded antibody (*Science*, 242, 423 (1988)), a dimerized variable region fragment (*Nature Biotechnol.*, 15, 629 (1997)), a disulfide antibody fragment (disulfide stabilized variable region fragment) (*Molecular Immunol.*, 32, 249 (1995)), a peptide comprising CDR (*J. Biol. Chem.*, 271, 2966 (1996)), etc.; and the like.

Furthermore, a peptide and a protein having an affinity to a carbohydrate obtained by phage display or the like are also included.

The low molecular weight compound having an affinity to a carbohydrate include serotonin, phenyl borate and the like. Furthermore, it also includes a carrier to which a functional group having an affinity to a carbohydrate is bound. Serotonin is a low molecular weight compound having an affinity to sialic acid.

An antibody having a long carbohydrate has a lower hydrophobicity due to the number of hydroxyl group being large, while an antibody having a short carbohydrate has a higher hydrophobicity due to that the number of hydroxyl groups is small. The functional group having an affinity to a carbohydrate includes a hydrophobic functional group such as a phenyl group, a butyl group, an octyl group and the like. As a result of using a carrier to which any of these functional groups is bound, an antibody composition having a carbohydrate structure in which less sugars are added to the non-reducing end shown in the above formula (I) can be purified and obtained.

An antibody composition having a desired property can be purified by conducting chromatography or the like using an apparatus wherein a substance having an affinity to a carbohydrate is bound directly or indirectly to a carrier such as a resin, a film or the like.

The carrier includes a synthetic resin polymer, and is preferably an acrylic synthetic resin polymer or a vinyl synthetic resin polymer, and more preferably a polyacrylate ester.

The desired property in the present invention includes an effector activity such as CDC activity, ADCC activity, etc., in vivo stability and the like.

CDC activity is an activity of making a hole in a membrane of a microorganism or working so as to be eaten by macrophage or neutrophil through binding of a complement to an antibody which is bound to an antigen to form a membrane-impaired protein complex. ADCC activity is an activity wherein an antibody which is bound to a tumor cell or the like activates an effector cell such as a killer cell, a natural killer cell, an activated macrophage or the like via binding of the Fc region of the antibody to an Fc receptor present on the surface of the effector cell to thereby impair the tumor cell or the like.

Furthermore, the desired properties include homogeneity of the carbohydrate structure of an antibody.

The desired properties described above are derived from the carbohydrate structure of an antibody. When the carbohydrate structure which is bound to the Fc region of an antibody in the antibody composition has higher ratios of a carbohydrate structure having no fucose bound to GlcNAc at reducing end via an α1,6-bond and a carbohydrate structure having bisecting GlcANc, the antibody composition shows higher ADCC activity. Also, when the carbohydrate structure bound to the Fc region of an antibody in the antibody composition has a higher ratio of a carbohydrate structure having galactose, the antibody composition shows higher CDC and ADCC activities. The higher the ratio of an carbohydrate structure having an increased content of sialic acid in the antibody composition is, the more stable in vivo the antibody composition is. Moreover, the higher the ratio of a carbohydrate structure having no Neu5Gc among sialic acid in the antibody composition is, the lower the immunogenicity of the antibody composition is.

Therefore, an antibody composition having a desired property can be purified by carrying out purification using a substance which specifically recognizes these carbohydrate structures.

Moreover, an antibody composition having a desired property can be further purified by combining the purification process of the present invention.

According to the purification process of the present invention, an antibody composition can be purified from body fluid such as serum, etc., culture medium in which antibody-producing cells have been cultured, and the like. The culture medium is preferably a solution obtained by removing cells beforehand, and more preferably a solution in which no glycopeptide is present. Examples include a solution roughly purified by a known process for purifying an antibody composition such as purification with protein A, etc., and the like. Furthermore, the culture medium in which antibody-producing cells have been cultured is preferably a culture medium in which they have been cultured in a serum-free or protein-free medium.

The processes for purification, evaluation, and employment according to the present invention will be specifically explained below.

1. Purification of Antibody Composition (1) Purification by Lectin Chromatography Lectin chromatography is affinity chromatography using the character that lectin specifically binds to a carbohydrate.

The kind of the lectin used for purifying an antibody composition having a desired property can be selected depending on the carbohydrate structure of the antibody.

When the desired property is CDC activity, a lectin having an affinity to galactose can be used. The lectin having an affinity to galactose includes RCA, and is preferably RCA120.

When the desired property is ADCC activity, a lectin having an affinity to fucose or bisecting GlcNAc can be used. The lectin having an affinity to fucose includes LCA, and is preferably LA-LCA (manufactured by Honen Corporation). The lectin having an affinity to bisecting GlcNAc includes WGA, PHA-E$_4$ and the like, and is preferably LA-WGA and LA-PHA-E$_4$ (both manufactured by Honen Corporation).

When the carbohydrate structure of an antibody in the antibody composition having a desired property is apparent, a lectin is selected with reference to the above specificity of lectins.

When the carbohydrate structure of an antibody in the antibody composition having a desired property is unknown, a lectin having a binding ability can be selected by carrying out a dot blot method (*Analytical Biochemistry*, 204(1), 198 (1992)) or the Western blotting (*Practice and Study of Legal Medicine*, 37, 155 (1994)) using a lectin labeled with biotin, fluorescein isothiocyanate, horseradish peroxidase or the like.

In the glycopeptide having a large number of carbohydrates in one molecule, the glycopeptide may be difficult to elute due to its stronger binding to a lectin. In this case, the glycopeptide may be easily eluted by increasing the sugar concentration of the eluent, but it is more preferable to select other lectin which weakly binds to the glycopeptide.

Examples of a column for the lectin chromatography includes HiTrap ConA, HiTrap Lentil Lectin (LCA), HiTrap Wheat Germ Lectin (WGA) (all manufactured by Pharmacia) and the like. In addition, a column which immobilized a carrier to which a lectin isolated from a biological sample such as a microorganism, a plant, an animal or the like may be used. The carrier includes agarose, a polymer of an acrylic synthetic resin and the like, and a polymer of acrylate ester is preferable. When a high-performance liquid chromatography (hereinafter referred to as "HPLC") system is used, any commercially available HPLC system can be used. Examples include LC-6A (manufactured by Shimadzu Corporation) and the like.

One example of the purification process using an HPLC system is shown below. As an eluent, 10 to 100 mmol/l tris-sulfate buffer, 10 to 100 mol/l acetic acid-sodium acetate buffer or the like is used. The pH is preferably from about 7 to 8. First, a column is sufficiently equilibrated with an initial eluent such as 10 to 100 mmol/l tris-sulfate buffer, 10 to 100 mol/l acetic acid-sodium acetate buffer or the like. A sample is passed through the column in an HPLC system and eluted using 10 to 100 mmol/l tris-sulfate buffer, 10 to 100 mol/l acetic acid-sodium acetate buffer containing an eluting sugar. The eluting sugar varies depending on a lectin. For example, in the case of ConA column, 0.02 to 0.5 mol/l methyl $\alpha$-D-glucoside or 0.02 to 0.5 mol/l methyl $\alpha$-D-mannoside is used as the eluting sugar. Elution is carried out by a stepwise method or a gradient method. Proteins can be detected by a method such as ultraviolet absorption, electrophoresis or the like.

(2) Purification by Hydrophobic Chromatography

Hydrophobic chromatography is a technique of separating proteins based on a difference in hydrophobicity of proteins. In general, the chromatography is used for separating a target protein utilizing a difference in hydrophobicity between the target protein and contaminated proteins.

When hydrophobic chromatography of the same protein is carried out, a difference in carbohydrate structure or dimer content of the protein may be detected based on a difference in elution time. This is because the difference in hydrophobicity occurs with a change of the stereochemical structure of the protein.

A column for the hydrophobic chromatography may be any commercially available column for hydrophobic chromatography. Examples include HiTrap 16/10 Phenyl (manufactured by Pharmacia), TSK-gel Phenyl-5PW (manufactured by Tosoh corporation) and the like.

When an HPLC system is used, any commercially available HPLC system can be used. Examples include LC-6A (manufactured by Shimadzu Corporation) and the like.

One example of the purification process using an HPLC system is shown below wherein an HPLC system is employed. As an eluent, 10 to 100 mmol/l citric acid-glycine buffer, 10 to 100 mol/l sodium sulfate buffer or the like is used. The pH is preferably from about 5 to 8, preferably about 7. First, a column is sufficiently equilibrated with an initial eluent such as 10 to 100 mmol/l citric acid-glycine buffer, 10 to 100 mol/l sodium sulfate buffer or the like containing 0.5 to 1 mol/l ammonium sulfate. A sample is passed through the column in an HPLC system and eluted using an eluent such as 10 to 100 mmol/l citric acid-glycine buffer, 10 to 100 mol/l sodium sulfate buffer or the like. Elution is carried out by a stepwise method or a gradient method. Proteins can be detected by a method such as ultraviolet absorption, electrophoresis or the like.

2. Evaluation of Antibody Composition

The following methods can be used for measuring activities of the antibody composition obtained by the above method 1 and analyzing the carbohydrate which is bound to the antibody composition.

(1) Evaluation of Activity of Antibody Composition

The binding activity of the antibody composition purified in the above 1 to an antigen and the binding activity to an antigen-positive culture cell line can be measured by ELISA, a fluorescent antibody method (*Cancer Immunol. Immunother.*, 36, 373 (1993)) or the like. The cytotoxic activity against an antigen-positive culture cell line can be evaluated by measuring CDC activity, ADCC activity or the like (*Cancer Immunol. Immunother.*, 36, 373 (1993)). Furthermore, safety and therapeutic effects on human can be evaluated using an appropriate model of animal species relatively near to human, such as *Macaca fascicularis* or the like.

(2) Analytical Method of Carbohydrate of Antibody Composition

Examples of an analytical method of the carbohydrate structure of an antibody composition include a two-dimensional carbohydrate map method (*Anal. Biochem.*, 171, 73 (1988); *Experimental Method in Biochemistry*, 23, "Glycoprotein Carbohydrate Studying Method" (Japan Scientific Societies Press), edited by Reiko Takahashi (1989)). The two-dimensional carbohydrate map method is a method in which the retention time or elution position of the carbohydrate on a reverse-phase chromatography and the retention time or elution position of the carbohydrate on a normal-phase chromatography are plotted at X-axis and Y-axis, respectively, and the plots are compared with the results of known carbohydrates to thereby presume a carbohydrate structure.

Specifically, carbohydrates are freed from an antibody composition by hydrazinolysis and are subjected to fluorescent labeling with 2-aminopyridine (hereinafter referred to as "PA") (*J. of Biochem.*, 95, 197 (1984)). Thereafter, the carbohydrates are separated from an excess PA-labeling reagent or the like by gel filtration and subjected to reverse-phase chromatography. Furthermore, normal-phase chromatography is carried out on each peak of separated carbohydrates. Based on these results, a carbohydrate structure can be estimated by plotting the data on a two-dimensional carbohydrate map (*Anal. Biochem.*, 171, 73 (1988)).

Furthermore, the carbohydrate structure estimated by two-dimensional carbohydrate map method can be confirmed by measuring mass spectrometry such as Matrix-assisted laser desorption iniozation-time of flight-mass spectrometry (MALDI-TOF-MS) or the like of each carbohydrate.

3. Method of Using Antibody Composition (1) Medicament Comprising as an Active Ingredient Antibody Obtained by the Purification Process of the Present Invention The characteristics of the antibody composition purified by the above method 1 are confirmed by the evaluation method of the above 2.

LCA has an affinity to the structure in which L-fucose is bound to a GlcNAc residue via an $\alpha 1,6$-bond. Thus, an antibody which has or does not have fucose bound to GlcNAc at a reducing end side via an $\alpha 1,6$-bond in the carbohydrate structure bound to the Fc region of the antibody can be separated and purified by purification with LCA.

Moreover, WGA and PHA-$E_4$ have an affinity to bisecting GlcNAc. Thus, an antibody which has or does not have bisecting GlcNAc at a non-reducing end side in the carbohydrate structure bound to the Fc region of the antibody can be separated and purified by purification with WGA or PHA-$E_4$.

An antibody composition comprising an antibody having a carbohydrate structure in which fucose is not bound to GlcNAc at a reducing terminal side obtained by purification with LCA and an antibody having a carbohydrate structure having bisecting GlcNAc at a non-reducing terminal side obtained by purification with WGA or PHA-$E_4$ have high ADCC activity.

The antibody having such a characteristic is useful for prevention and treatment of various diseases such as cancer, allergy, circulatory diseases, viral or bacterial infections and the like.

The general anticancer agents have a characteristic of inhibiting growth of cancer cells. However, the agent having high ADCC activity can treat cancers by impairing cancer cells, and therefore is more useful than the general anticancer agents.

Since allergic reaction is caused by the release of a mediator molecule from immunocytes, the allergic reaction can be suppressed by removing immunocytes using an antibody composition having high ADCC activity.

Examples of circulatory diseases include arteriosclerosis and the like. Balloon catheter is known as a method for treating arteriosclerosis. However, as a result, arterial cells may grow to cause restenosis. Circulatory diseases can be prevented or treated by inhibiting the growth of arterial cells using an antibody composition having high ADCC activity.

Also, various diseases including viral or bacterial infections can be prevented and treated by inhibiting the growth of the cells infected with virus or bacteria using an antibody composition having high ADCC activity.

Among the antibody compositions purified using LCA in the above 1(1), the antibody composition having a carbohydrate structure having fucose bound to GlcNAc at a reducing end via an $\alpha1,6$-bond has ADCC activity lower than the above-described antibody composition. The antibody composition having decreased ADCC activity is useful for prevention and treatment of autoimmune diseases from the viewpoint of suppressing increased immunoreaction in autoimmune diseases.

Among the antibody compositions purified by a hydrophobic chromatography in the above 1(2), the antibody having a large number of carbohydrate structures having galactose has high CDC and ADCC activities. Therefore, the antibody composition having such a property is useful for prevention and treatment of various diseases such as cancer, allergy, circulatory diseases, viral or bacterial infections and the like.

Among the antibody compositions purified by a hydrophobic chromatography in the above 1(2), the antibody composition comprising a small number of carbohydrate structures having galactose has CDC and ADCC activities lower than those of the antibody composition before the purification. The antibody composition having decreased CDC and ADCC activities is useful for prevention and treatment of autoimmune diseases from the viewpoint of suppressing increased immunoreaction in autoimmune diseases.

Moreover, the carbohydrate structures and the properties resulted from the carbohydrate structures may be combined. Specifically, the process for purifying such antibody composition includes a process using a combination of columns to which a substance having an affinity to a carbohydrate is immobilized and a process using a column prepared by mixing substances having different binding specificity to carbohydrates within the same column.

The above purified antibody composition can be administrated alone but in general, is preferably provided as a pharmaceutical formulation produced by any method well known in the technical field of manufacturing pharmacy through mixing with one or more pharmaceutically acceptable carriers.

It is preferable to use a route of administration which is most effective in carrying out a treatment. Examples include oral administration and parenteral administration such as buccal, airway, rectal, subcutaneous, intramuscular, intravenous administration and the like. Intravenous administration is preferable.

Examples of a dosage form include a spray, a capsule, a tablet, a granule, a syrup, an emulsion, a suppository, an injection, an ointment, a tape and the like.

Examples of a formulation suitable for oral administration include an emulsion, a syrup, a capsule, a tablet, a powder, a granule and the like.

A liquid preparation such as an emulsion and a syrup can be produced by using, as additives, water; saccharides such as sucrose, sorbitol, fructose, etc.; glycols such as polyethylene glycol, propylene glycol, etc.; oils such as sesame oil, olive oil, soybean oil, etc.; antiseptics such as p-hydroxybenzoic acid esters, etc.; flavors such as strawberry flavor, peppermint, etc.; and the like.

A capsule, a tablet, a powder, a granule and the like can be produced by using, as additives, a filler such as lactose, glucose, sucrose, mannitol, etc.; a disintegrating agent such as starch, sodium alginate, etc.; a lubricant such as magnesium stearate, talc, etc.; a binder such as polyvinyl alcohol, hydroxypropylcellulose, gelatin etc.; a surfactant such as fatty acid ester, etc.; a plasticizer such as glycerol, etc.; and the like.

Examples of a pharmaceutical preparation suitable for parenteral administration include an injection, a suppository, a spray and the like.

An injection is prepared using a carrier such as a salt solution, a glucose solution, a mixture of both of them or the like.

A suppository is prepared using a carrier such as cacao butter, hydrogenated fat, carboxylic acid or the like.

Also, a spray is prepared using the antibody of the present invention as such or using a carrier which does not stimulate the buccal or airway mucous membrane of a patient and can facilitate absorption of the antibody or the antibody fragment by dispersing it as fine particles.

Examples of the carrier include lactose, glycerine and the like. Depending on the properties of the antibody and the used carrier, it is possible to produce a pharmaceutical preparation such as aerosol, dry powder or the like. In addition, the components exemplified as additives for the oral preparation can also be added to the parenteral preparation.

Although the dose and the frequency of the administration vary depending on the objective therapeutic effect, administration method, therapeutic term, age, body weight and the like, it is administered to an adult at a dose of 0.01 to 20 mg/kg per day.

(2) Diagnosis Method Using a Substance having an Affinity to a Carbohydrate Binding to an Antibody Diagnosis of various diseases can be effected by extracting a biological sample from a human body and detecting or determining quantitatively an antibody in the biological sample using a substance having an affinity to a carbohydrate. Moreover, by detecting or determining quantitatively an antibody in a human body, change of human biological functions, progress of diseases, and the like can be diagnosed.

The method comprises packing a column with a carrier to which a substance having an affinity to a carbohydrate binding to an antibody in the present invention is immobilized. A biological sample collected from a human body is passed through the column and the ratio of various carbohydrate structures binding to an antibody is detected or determined quantitatively. By combining a column packed with a carrier to which a substance having an affinity to a carbohydrate binding to an antibody and a column packed with protein A having a property of specifically adsorbing an antibody, diseases such as rheumatism can be diagnosed more specifically and conveniently.

Specifically, diagnosis of rheumatism which is an autoimmune disease is exemplified.

As described above, an antibody composition having a desired property can be purified according to the present invention. Moreover, the medicament comprising an antibody composition obtained by the purifying method of the present invention as an active ingredient is useful for diagnosis of human various diseases owing to its desired property. Furthermore, various diseases can be diagnosed by using a process similar to the process for purifying an antibody composition from a biological sample.

The present invention will be explained based on Examples below, but the scope of the present invention is not limited thereto.

EXAMPLE 1

Fractionation of an antibody composition comprising a large amount of a fucose-bound carbohydrate:

(1) Fractionation of an Antibody Composition by Lectin Chromatography

An anti-hIL-5Rα CDR-grafted antibody composition was purified using a lectin binding to a carbohydrate having fucose.

First, an expression vector for anti-hIL-5Rα CDR-grafted antibody which is produced according to the method described in WO97/10354 was introduced into a rat myeloma YB2/0 cell to obtain a cell which produces the anti-hIL-5Rα CDR-grafted antibody composition. The cell was cultured in a culture medium and then the anti-hIL-5Rα CDR-grafted antibody composition was purified from the medium according to the method described in WO97/10354.

Next, a solution comprising the anti-hIL-5Rα CDR-grafted antibody composition obtained in the above was passed through a lectin column (LA-LCA, 4.6×150 mm, manufactured by Honen Corporation). Using LC-6A manufactured by Shimadzu Corporation as an HPLC system, the solution was passed through the column at a flow rate of 0.5 ml/minute and at a room temperature as the column temperature. The column was equilibrated with 50 mM tris-sulfate buffer (pH 7.3), and the purified anti-hIL-5Rα CDR-grafted antibody composition was injected and then eluted by a linear gradient (60 minutes) of 0 M to 0.2 M of α-methylmannoside (manufactured by Nacalai Tesque) in 50 mM tris-sulfate buffer (pH 7.3). The anti-hIL-5Rα CDR-grafted antibody composition was fractionated into a non-adsorbed fraction and an absorbed fraction (FIG. 1).

(2) Measurement of Binding Activity (ELISA)

The non-adsorbed fraction and a part of the adsorbed fraction shown in FIG. 1 were collected, and the binding activity to hIL-5Rα was measured by ELISA. Each 50 μl of a solution of anti-hIL-5Rα mouse antibody KM1257 described in WO97/10354 diluted to a concentration of 10 μg/ml with PBS was dispensed into each well of a 96-well plate for ELISA (manufactured by Greiner), followed by reaction at 4° C. for 20 hours. After the reaction, 1% BSA-PBS was added in an amount of 100 μl/well, followed by reaction at room temperature for 1 hour to block remaining active groups. The 1% BSA-PBS was discarded and a solution of soluble hIL-5Rα described in WO97/10354 diluted to 0.5 μg/ml with 1% BSA-PBS was added in an amount of 50 μl/well, followed by reaction at 4° C. for 20 hours. After the reaction, each well was washed with Tween-PBS and then a variously diluted solution of the culture supernatant of the transformant or the purified humanized CDR-grafted antibody composition was added in an amount of 50 μl/well, followed by reaction at room temperature for 2 hours. After the reaction, each well was washed with Tween-PBS and then a solution of a peroxidase-labeled goat anti-human IgG (H&L) antibody (manufactured by American Qualex) diluted by 3000 times with 1% BSA-PBS was added as the second antibody solution in an amount of 50 μl/well, followed by reaction at room temperature for 1 hour. After the reaction, each well was washed with Tween-PBS and then an ABTS substrate solution (a solution obtained by dissolving 0.55 g of ammonium 2,2'-azino-bis(3-ethylbenzothiazoline-6-sulfonate) in 1 L of 0.1 M citric acid buffer (pH 4.2) and, immediately before use, adding hydrogen peroxide in an amount of 1 μl/ml) was added in an amount of 50 μl/well to develop color. Then, absorbance at 415 nm (OD415) was measured.

Figure 2:
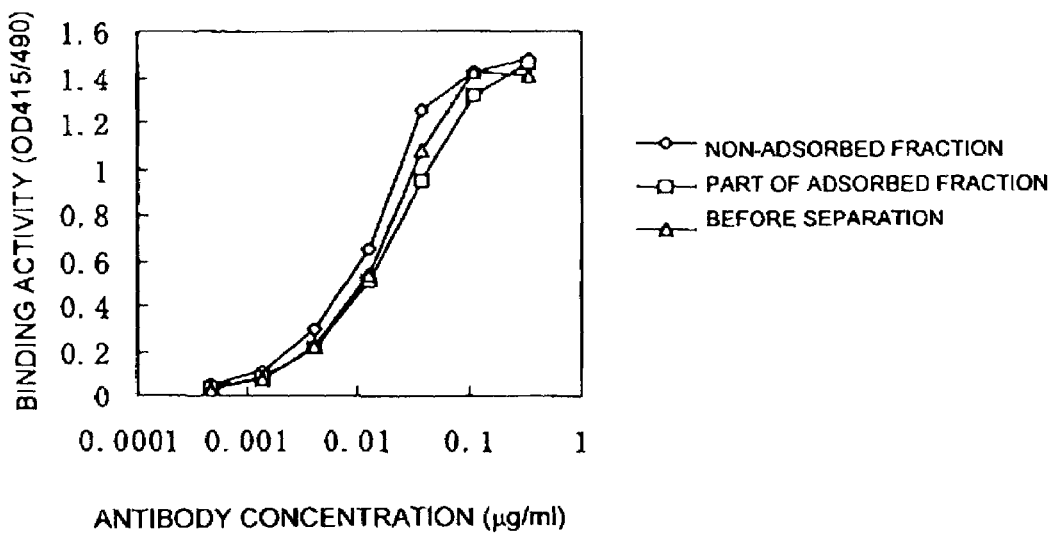
FIG. 2 is a drawing obtained by measuring binding activities to hIL-5Rα of a non-adsorbed fraction and a part of an adsorbed fraction obtained by fractionating an anti-hIL-5Rα CDR-grafted antibody composition using a lectin binding to a carbohydrate having fucose and the anti-hIL-5Rα CDR-grafted antibody composition before separation, while the antibody concentration being changed. The ordinate and the abscissa indicate the binding activity toward hIL-5Rα and the antibody concentration, respectively. The symbols ◇, ☐ and Δ indicate the non-adsorbed fraction, the part of an adsorbed fraction and the anti-hIL-5Rα CDR-grafted antibody composition before separation, respectively.

As a result of the measurement, the non-adsorbed fraction and the part of the adsorbed fraction showed a binding activity similar to that of the anti-hIL-5Rα CDR-grafted antibody composition before the separation (FIG. 2).

(3) In Vivo Cytotoxic Activity (ADCC Activity)

ADCC activities of the non-adsorbed fraction and the part of the adsorbed fraction were measured, respectively. First, a target cell solution was prepared. A mouse T cell line CTLL-2(h5R) expressing hIL-5R α-chain and β-chain described in WO97/10354 was cultured in RPMI1640-FBS (10) medium to prepare the culture to give a concentration of $1 \times 10^6$ cells/0.5 ml, and 3.7 MBq equivalents of a radioactive substance $Na_2^{51}CrO_4$ was added thereto, followed by reaction at 37° C. for 1.5 hours to thereby radio-label the cell. After the reaction, the cell was washed three times by suspending into RPMI1640-FBS(10) medium and centrifuging, and then re-suspended into the medium and incubated at 4° C. for 30 minutes in ice to dissociate the radioactive substance spontaneously. After centrifugation, a target cell solution was obtained by incorporating with 5 ml of RPMI1640-FBS(10) medium to prepare a solution of $2 \times 10^5$ cells/ml.

Next, an effector cell solution was prepared. Healthy human venous blood was collected in an amount of 50 ml and, after the addition of 0.5 ml of heparin sodium (manufactured by Takeda Chemical Industries, Ltd.), the mixture was gently stirred. The mixture was centrifuged using Polymorphprep (manufactured by Nycomed Pharma AS) according to the manufacture's instructions to separate a mononuclear cell layer. The layer was washed by centrifuging three times in RPMI1640-FBS(10) medium and then re-suspended into the medium at a concentration of $9\times10^6$ cells/well to prepare an effector cell solution.

To each well of a 96-well U-shaped bottom plate (manufactured by Falcon), 50 µl ($1\times10^4$ cells/well) of a target cell prepared in the above was dispensed. Then, 100 µl ($9\times10^5$ cells/well) of the prepared effector cell solution was added thereto (the ratio of the effector cell to the target cell was 90:1). Furthermore, each of various anti-hIL-5Rα CDR-grafted antibodies was added to give a final concentration of 0.001 to 0.1 µg/ml, followed by reaction at 37° C. for 4 hours. After the reaction, the plate was centrifuged and the amount of $^{51}Cr$ in the supernatant was measured by a y-counter. A spontaneously dissociated amount of $^{51}Cr$ was determined by measuring the amount of $^{51}Cr$ in the supernatant obtained by conducting a similar operation to the above using the medium alone instead of the effector cell solution and antibody solution. The total dissociated amount of $^{51}Cr$ was determined by measuring the amount of $^{51}Cr$ in the supernatant obtained by conducting a similar operation to the above using the medium alone instead of the antibody solution and 1 N hydrochloric acid instead of the effector cell solution. ADCC activity was determined according to the following equation.

$$ADCC \text{ activity} (\%) = \frac{^{51}Cr \text{ amount in sample supernatant} - \text{spontaneously released } ^{51}Cr \text{ amount}}{\text{total released } ^{51}Cr \text{ amount} - \text{spontaneously released } ^{51}Cr \text{ amount}} \times 100$$

Figure 3:
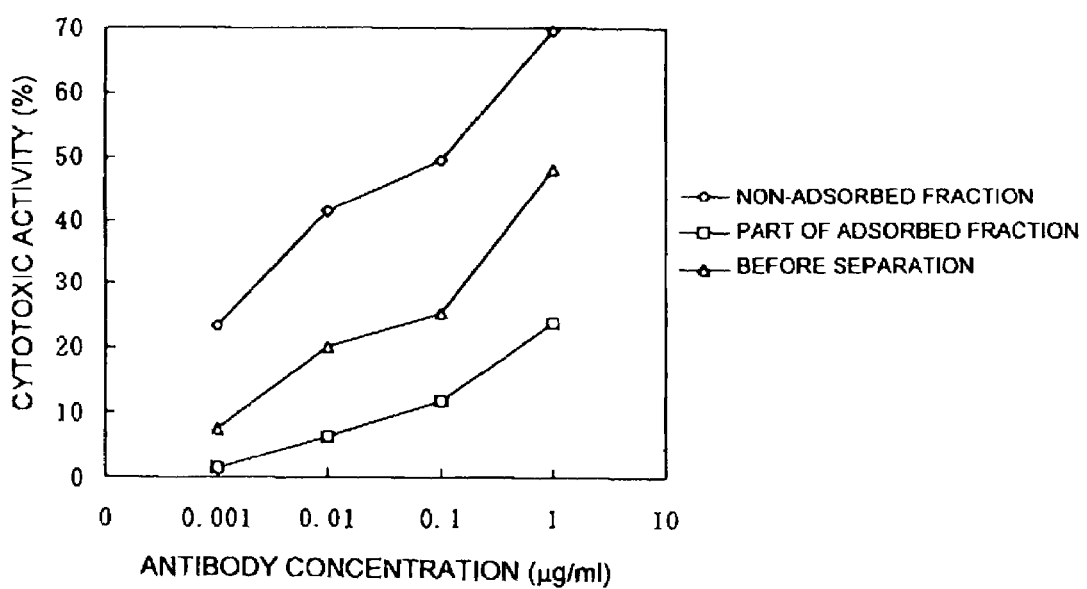
FIG. 3 is a drawing showing ADCC activities to an hIL-5R-expressing mouse T cell line CTLL-2(h5R) of a non-adsorbed fraction and a part of an adsorbed fraction obtained by fractionating an anti-hIL-5Rα CDR-grafted antibody composition using a lectin binding to a carbohydrate having fucose and the anti-hIL-5Rα CDR-grafted antibody before separation. The ordinate and the abscissa indicate the cytotoxic activity and the antibody concentration, respectively. The symbols ◇, ☐ and Δ indicate the non-adsorbed fraction, the part of an adsorbed fraction and the anti-hIL-5Rα CDR-grafted antibody composition before separation, respectively.

The results are shown in FIG. 3. The non-adsorbed fraction had ADCC activity higher than the anti-hIL-5α CDR-grafted antibody composition before separation, and the part of the adsorbed fraction showed ADCC activity lower than the anti-hIL-5Rα CDR-grafted antibody composition before separation.

(4) Carbohydrate Analysis

Figure 4:
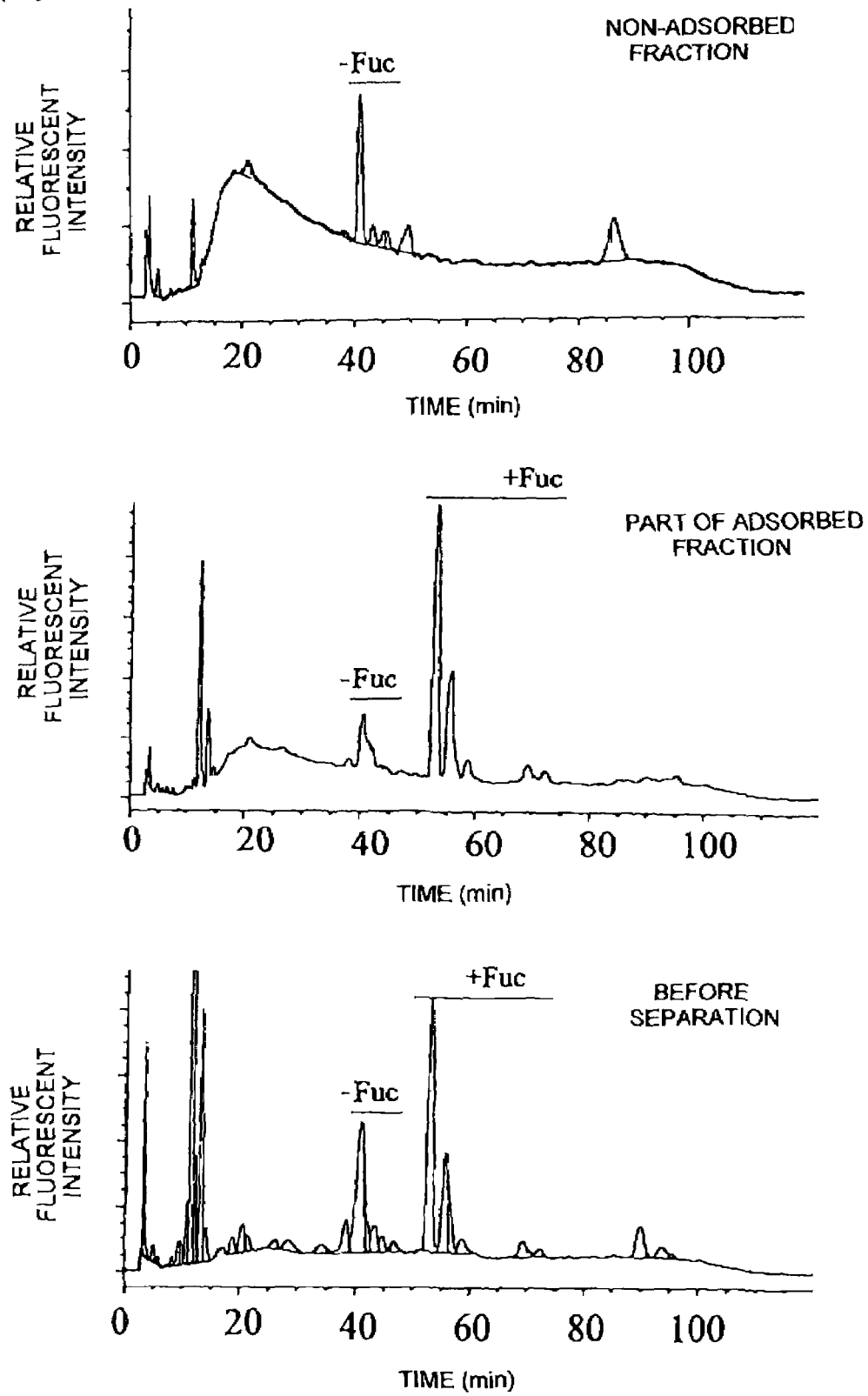
FIG. 4 is a drawing showing elution obtained by analyzing each of PA-labeled carbohydrates prepared from a non-adsorbed fraction and a part of an adsorbed fraction obtained by fractionating an anti-hIL-5Rα CDR-grafted antibody composition using a lectin binding to a carbohydrate having fucose and the anti-hIL-5Rα CDR-grafted antibody composition before separation on reverse phase HPLC. The upper figure, the middle figure and the lower figure are drawings showing elutions of the non-adsorbed fraction, the part of the adsorbed fraction and the anti-hIL-5Rα CDR-grafted antibody composition before separation, respectively. The ordinate and the abscissa indicate the relative fluorescent intensity and the elution time, respectively. In the drawings, "–Fuc" and "+Fuc" indicate carbohydrates having no fucose and carbohydrates having fucose, respectively.

The non-adsorbed fraction and the part of the adsorbed fraction were subjected to hydrazinolysis to cleave the carbohydrates from the proteins (*Method in Enzymology*, 83, 263 (1982)). After removal of hydrazine, N-acetylation was conducted by adding an aqueous ammonium acetate solution and acetic anhydride. After lyophillization, fluorescent labeling was conducted with PA (*J. of Biochem.*, 95, 197 (1984)). The fluorescence-labeled carbohydrates (PA-labeled carbohydrates) were separated from excess reagents by Surperdex peptide HR 10/30 column (manufactured by Pharmacia). The carbohydrate fraction was exsiccated in a centrifugal concentrating apparatus to prepare purified PA-labeled carbohydrates. Next, the purified PA-labeled carbohydrates were subjected to reverse-phase HPLC analysis using CLC-ODS column (manufactured by Shimadzu Corporation) (FIG. 4). The PA-labeled carbohydrates were eluted in the range of 39 minutes to 75 minutes. Based on the calculation from the peak areas, the carbohydrate having no fucose was 100% in the non-adsorbed fraction, while the carbohydrate having no fucose was 18% in the part of the adsorbed fraction. The carbohydrate having no fucose was 37% in the anti-hIL-5Rα CDR-grafted antibody composition before separation. Thus, an antibody composition comprising a larger amount of carbohydrate having no fucose and an antibody composition comprising a smaller amount of carbohydrate having no fucose than that contained in the anti-hIL-5Rα CDR-grafted antibody before separation can be separated each other and purified using a lectin column binding to a carbohydrate having fucose.

EXAMPLE 2

Fractionation of an antibody composition comprising a large amount of a bisecting GlcNAc-bound carbohydrate:

(1) Fractionation of an Antibody Composition by Lectin Chromatography

An anti-hIL-5Rα CDR-grafted antibody composition was purified using a lectin binding to a carbohydrate having bisecting GlcNAc.

First, an expression vector for anti-hIL-5Rα CDR-grafted antibody produced according to the method described in WO97/10354 was introduced into a rat myeloma YB2/0 cell to obtain a cell which produces the anti-hIL-5Rα CDR-grafted antibody composition. The cell was cultured in a culture medium and then the anti-hIL-5Rα CDR-grafted antibody composition was purified from the medium according to the method described in WO97/10354.

Next, a solution containing the anti-hIL-5Rα CDR-grafted antibody composition purified in the above was passed through a lectin column (LA-WGA, 4.6×150 mm, manufactured by Honen Corporation). Using LC-6A manufactured by Shimadzu Corporation as an HPLC system, the solution was passed through the column at a flow rate of 0.5 ml/minute and at room temperature as the column temperature. The column was equilibrated with 50 mM tris-sulfate buffer (pH 7.3), and the purified anti-hIL-5Rα CDR-grafted antibody composition was injected and then eluted by a linear gradient (60 minutes) of 0 M to 0.2 M of GlcNAc (manufactured by Junsei Chemical Co., Ltd.) in 50 mM tris-sulfate buffer (pH 7.3). The anti-hIL-5Rα CDR-grafted antibody composition was separated into a fraction eluted between 2 to 5 minutes and a fraction eluted between 8 to 12 minutes.

(2) Carbohydrate Analysis

Figure 5:
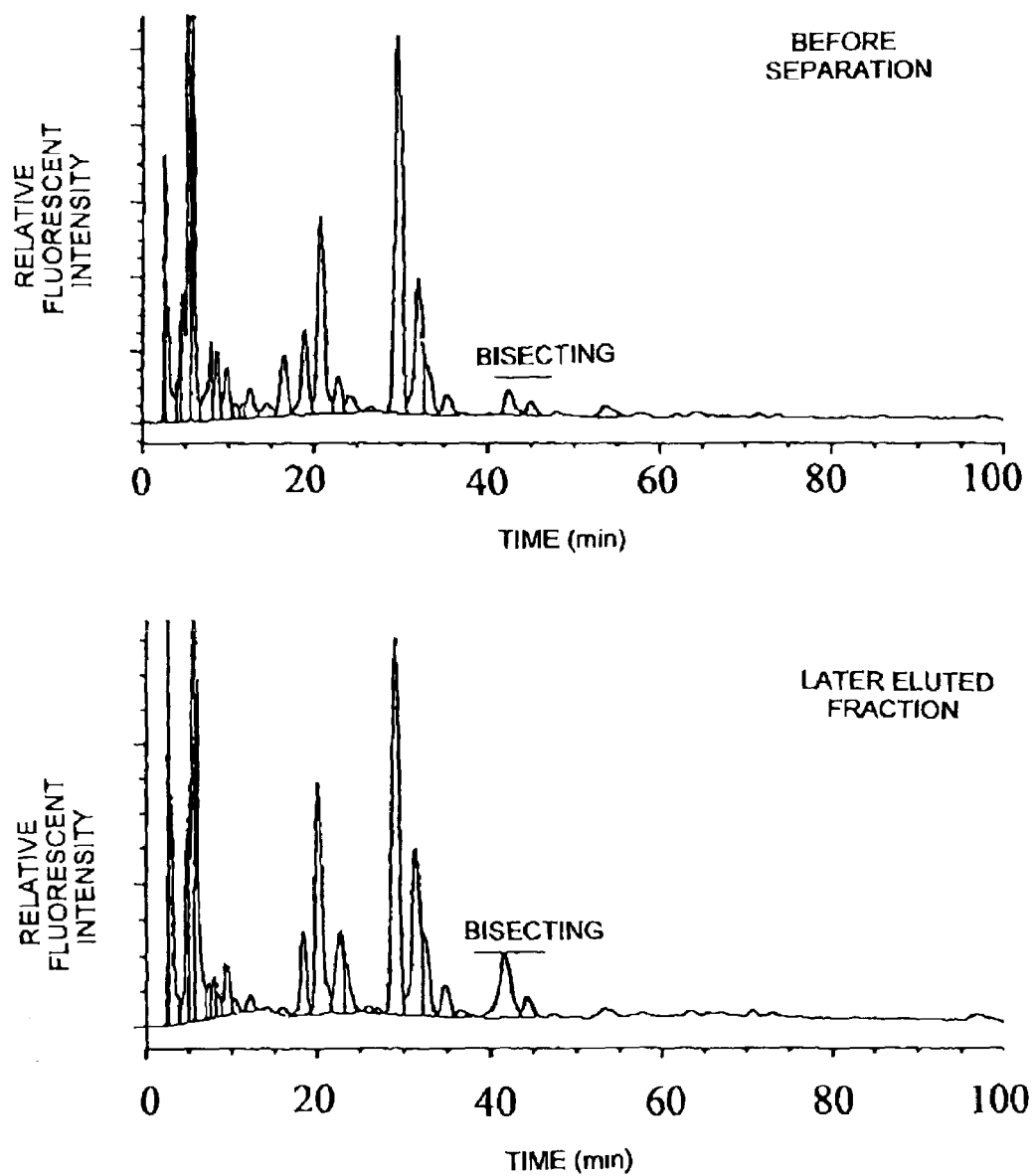
FIG. 5 is a drawing showing elution obtained by analyzing, with reverse phase HPLC, each of PA-labeled carbohydrates prepared from an anti-hIL-5Rα CDR-grafted antibody composition before separation and a later eluted fraction obtained by fractionating the anti-hIL-5Rα CDR-grafted antibody composition with chromatography using a lectin binding to a carbohydrate having bisecting GlcNAc. The upper figure and the lower figure are drawings showing elutions of the anti-hIL-5Rα CDR-grafted antibody composition before separation and the later eluted fraction, respectively. The ordinate and the abscissa indicate the relative fluorescent intensity and the elution time, respectively. In the drawings, "bisecting" indicates carbonates to which bisecting GlcNAc is bound.

Carbohydrates in the earlier eluted fraction and the later eluted fraction were analyzed by the method described in Example 1(4). The PA-labeled carbohydrate group was eluted in the range of 20 minutes to 50 minutes. As a result, the anti-hIL-5Rα CDR-grafted antibody composition of the later eluted fraction had a content of a carbohydrate having bisecting GlcNAc, increased from 6% to 12%, as compared with the anti-hIL-5Rα CDR-grafted antibody composition before purification and separation (FIG. 5).

EXAMPLE 3

Fractionation of an antibody composition comprising a small amount of a carbohydrate having fucose and a large amount of a bisecting GlcNAc-bound carbohydrate:

(1) Fractionation of an Antibody Composition by Lectin Chromatography

The antibody composition containing a large amount of a bisecting GlcNAc-bound carbohydrate obtained in Example 2 was separated into a non-adsorbed fraction and an adsorbed fraction in a similar manner to the method described in Example 1(1).

(2) Carbohydrate Analysis

Figure 6:
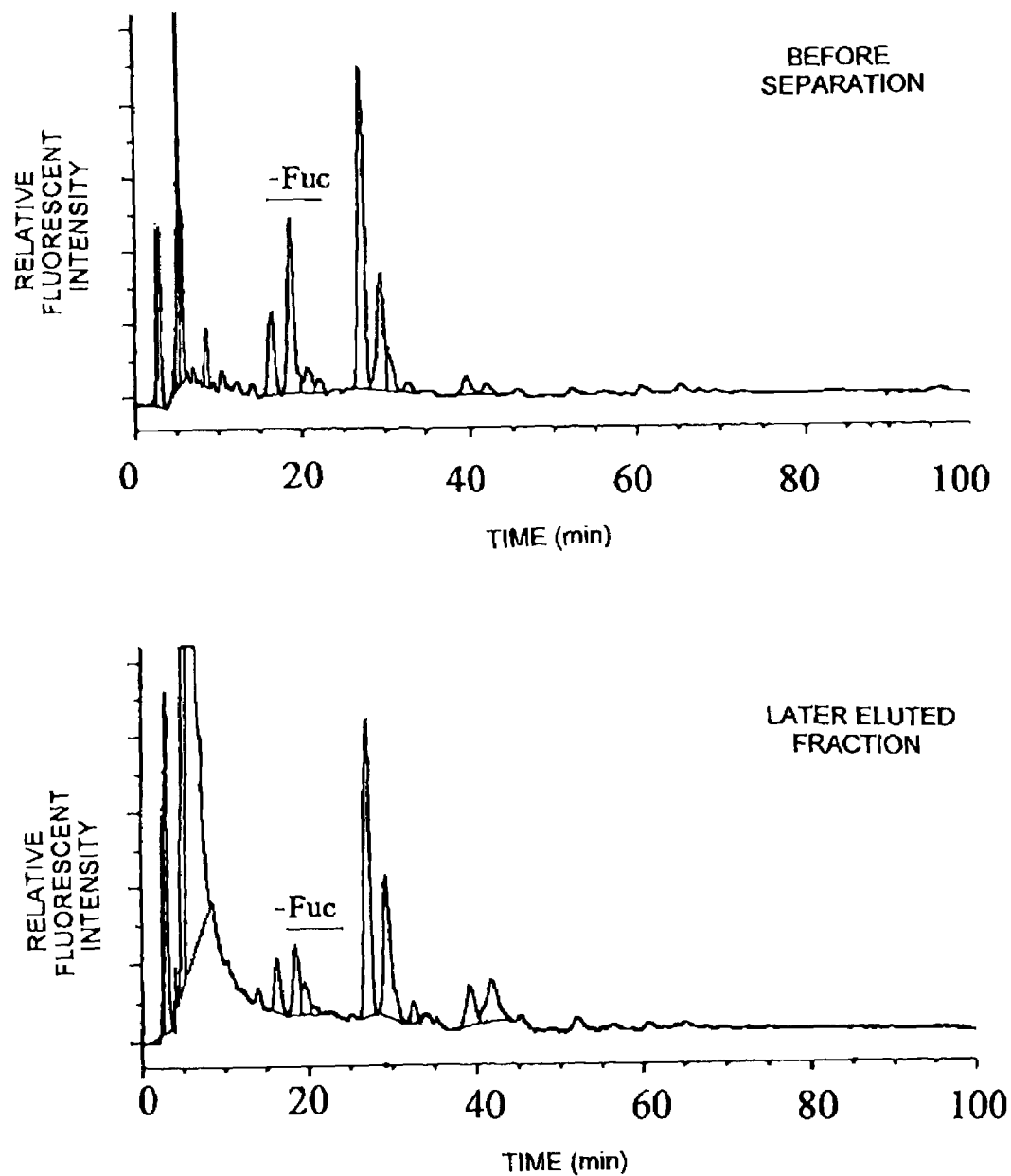
FIG. 6 is a drawing showing elution obtained by analyzing, with reverse phase HPLC, each of PA-labeled carbohydrates prepared from an anti-hIL-5Rα CDR-grafted antibody composition before separation and a later eluted fraction obtained by fractionating the anti-hIL-5Rα CDR-grafted antibody composition with chromatography using a lectin binding to a carbohydrate having bisecting GlcNAc, followed by further fractionation with chromatography using a lectin binding a carbohydrate having fucose. The upper figure and the lower figure are drawings showing elutions of the anti-hIL-5Rα CDR-grafted antibody composition before separation and the later eluted fraction, respectively. The ordinate and the abscissa indicate the relative fluorescent intensity and the elution time, respectively. In the drawings, "–Fuc" and "bisecting" indicate carbohydrates having no fucose and carbohydrates to which bisecting GlcNAc is bound, respectively.

Carbohydrates in the non-adsorbed fraction and the part of the adsorbed fraction were analyzed by the method described in Example 1(4). The PA-labeled carbohydrates were eluted in the range of 18 minutes to 45 minutes. As a result, the part of the adsorbed fraction had a content of a carbohydrate having no fucose, decreased from 29% to 15%, and a content of a bisecting GlcNAc-bound carbohydrate, increased from 5% to 18%, as compared with the anti-hIL-5Rα CDR-grafted antibody composition before separation (FIG. 6).

EXAMPLE 4

Fractionation of an antibody composition comprising a large amount of a galactose-bound carbohydrate:

(1) Fractionation of an Antibody Composition by Lectin Chromatography

An anti-hIL-5Rα CDR-grafted antibody composition was purified using hydrophobic chromatography.

First, an expression vector for anti-hIL-5Rα CDR-grafted antibody produced according to the method described in WO97/10354 was introduced into a rat myeloma YB2/0 cell to obtain a cell which produces the anti-hIL-5Rα CDR-grafted antibody composition. The cell was cultured in a culture medium and then the anti-hIL-5Rα CDR-grafted antibody composition was purified from the medium according to the method described in WO97/10354.

Next, a solution comprising the anti-hIL-5Rα CDR-grafted antibody composition purified in the above was passed through hydrophobic column Phenyl-5PW (manufactured by Tosoh Corporation). Using LC-6A manufactured by Shimadzu Corporation as an HPLC system, the solution was passed through the column at a flow rate of 1 ml/minute and at room temperature as the column temperature. The column was equilibrated with 20 mM sodium phosphate buffer (pH 6.0) containing 1 M ammonium sulfate, and the purified anti-hIL-5Rα CDR-grafted antibody composition was injected and then eluted by a linear gradient (60 minutes) to 20 mM sodium phosphate buffer (pH 6.0). The anti-hIL-5Rα CDR-grafted antibody composition was separated into an earlier eluted fraction (between 4 to 6 minutes) and a later eluted fraction (between 20 to 25 minutes).

(2) Carbohydrate Analysis

Figure 7:
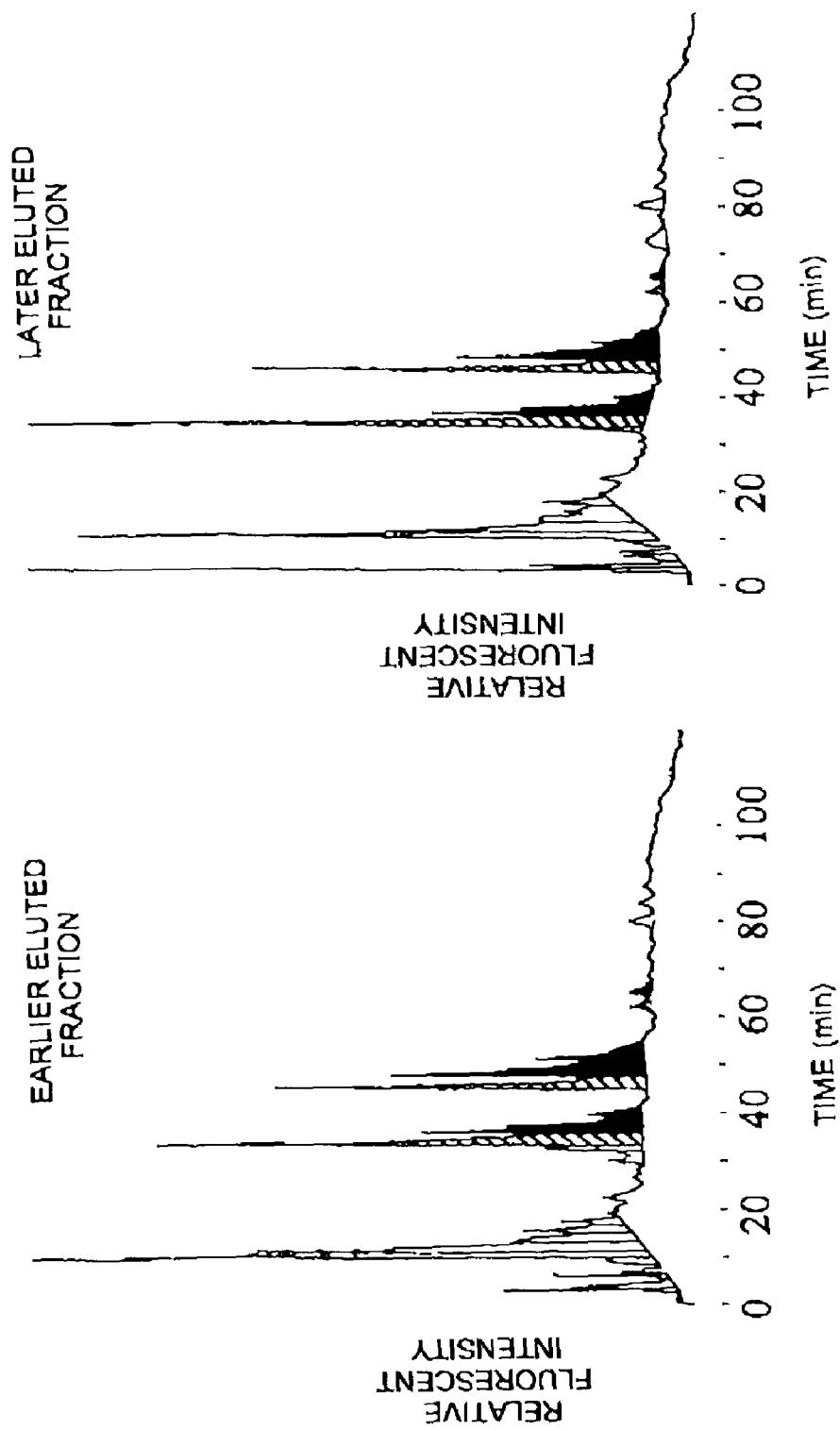
FIG. 7 is a drawing showing elution obtained by analyzing, with reverse phase HPLC, each of PA-labeled carbohydrates prepared from an earlier eluted fraction and a later eluted fraction. The left figure and the right figure are drawings showing elutions of the earlier eluted fraction and the later eluted fraction, respectively. The ordinate and the abscissa indicate the relative fluorescent intensity and the elution time, respectively. In the drawings, the shaded peaks and the black-filled peaks indicate carbonates having no galactose and carbonates to which galactose is bound, respectively.

Carbohydrates in the earlier eluted fraction and the later eluted fraction were analyzed by the method described in Example 1(4). The PA-labeled carbohydrate group was eluted in the range of 33 minutes to 70 minutes. As a result, a galactose-bound carbohydrate was 53% in the earlier eluted fraction, and a galactose-bound carbohydrate was 44% in the later eluted fraction (FIG. 7).

EXAMPLE 5

Fractionation of an antibody composition comprising a large amount of a fucose-bound carbohydrate:

(1) Fractionation of an Antibody Composition by Lectin Chromatography

An anti-hIL-5Rα CDR-grafted antibody composition was purified using a lectin binding to a carbohydrate having fucose.

First, an expression vector for anti-hIL-5Rα CDR-grafted antibody prepared according to the method described in WO97/10354 was introduced into a mouse myeloma NS0 cell to obtain a cell which produces the anti-hIL-5Rα CDR-grafted antibody composition. The cell was cultured in a culture medium and then the anti-hIL-5Rα CDR-grafted antibody composition was purified from the medium according to the method described in WO97/10354.

The anti-hIL-5Rα CDR-grafted antibody composition was fractionated into a non-adsorbed fraction and an absorbed fraction by treating the purified solution containing the anti-hIL-5Rα CDR-grafted antibody composition in a similar manner to the method described in Example 1(1).

(2) Measurement of Binding Activity (ELISA Method)

Figure 8:
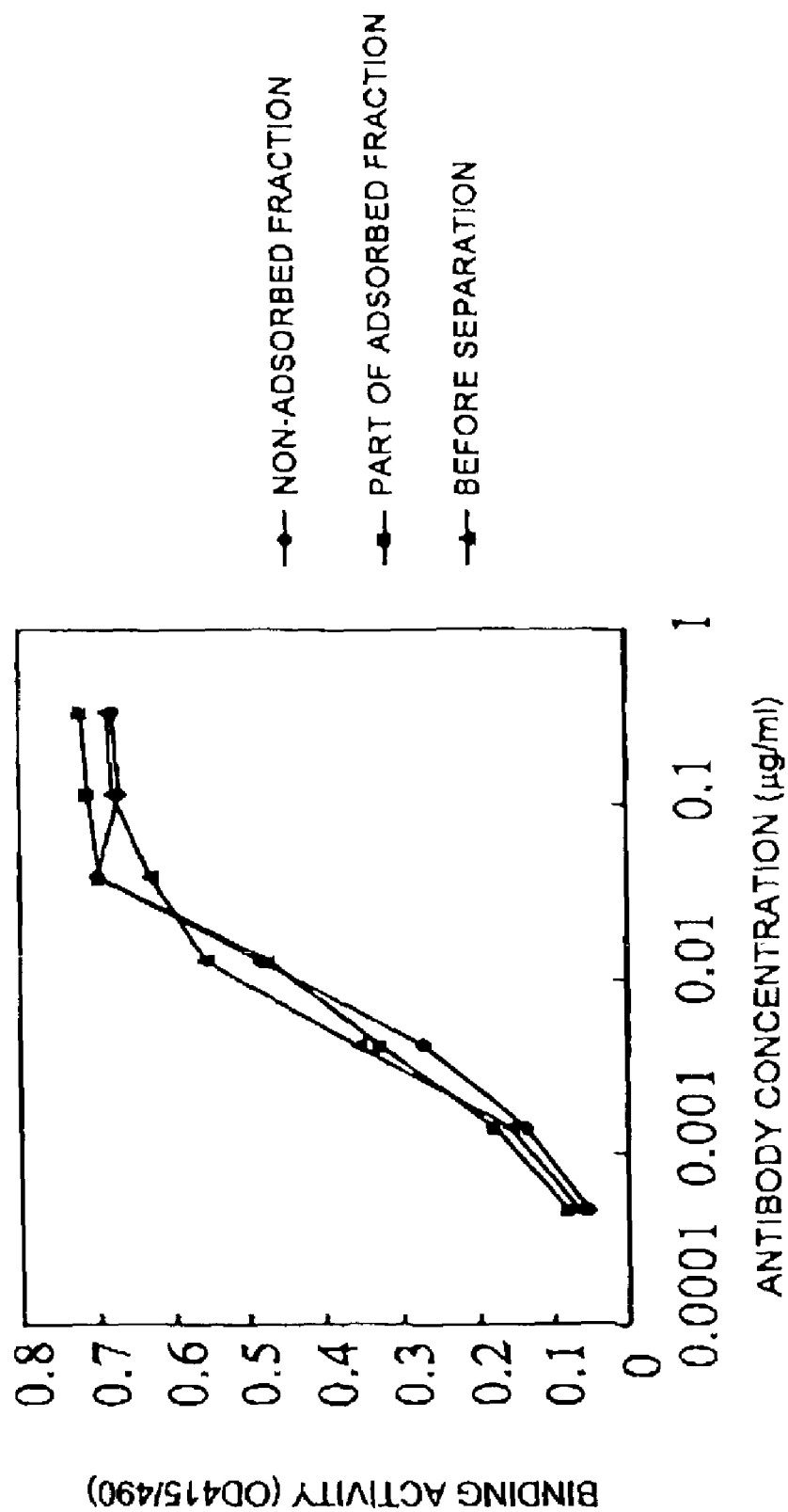
FIG. 8 is a drawing obtained by measuring binding activities to hIL-5Rα of a non-adsorbed fraction and a part of an adsorbed fraction obtained by fractionating an anti-hIL-5Rα CDR-grafted antibody composition using a lectin binding to a carbohydrate having fucose and the anti-hIL-5Rα CDR-grafted antibody composition before separation, while antibody concentration being changed. The ordinate and the abscissa indicate the binding activity to hIL-5Rα and the antibody concentration, respectively. The symbols ♦, ■ and ▲ indicate the non-adsorbed fraction, the part of the adsorbed fraction, and the anti-hIL-5Rα CDR-grafted antibody composition before separation, respectively.

The non-adsorbed fraction and the part of the adsorbed fraction were collected, and the binding activity to hIL-5Rα was measured by a method similar to the method described in Example 1(2). The non-adsorbed fraction and the part of the adsorbed fraction showed a binding activity similar to the anti-hIL-5Rα CDR-grafted antibody composition before separation (FIG. 8).

(3) In Vivo Cytotoxic Activity (ADCC Activity)

Figure 9:
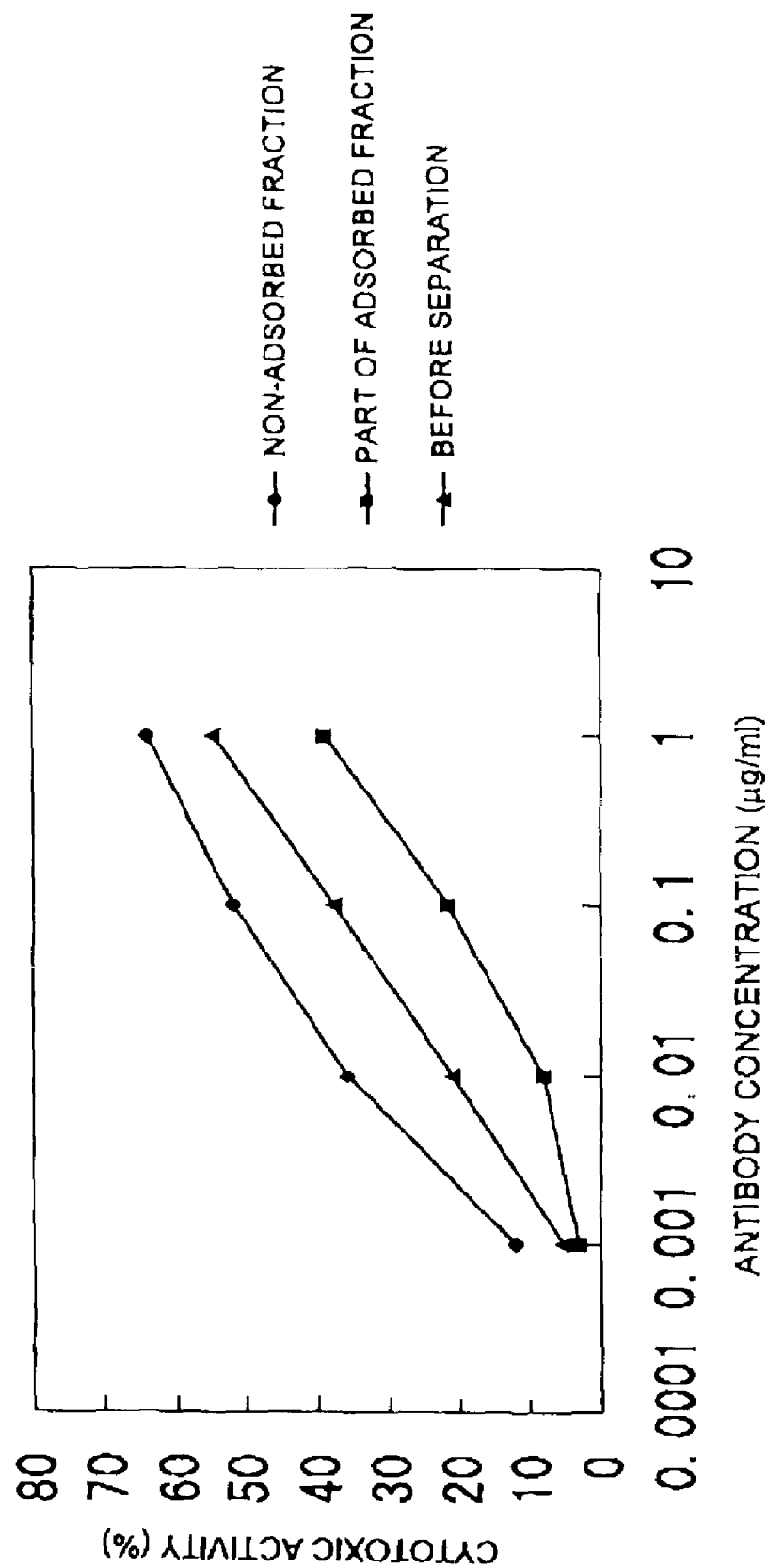
FIG. 9 is a drawing obtained by measuring ADCC activities to an hIL-5R-expressing mouse T cell line CTLL-2 (h5R) of a non-adsorbed fraction and a part of an adsorbed fraction obtained by fractionating an anti-hIL-5Rα CDR-grafted antibody composition using a lectin binding to a carbohydrate having fucose and the anti-hIL-5Rα CDR-grafted antibody composition before separation. The ordinate and the abscissa indicate the cytotoxic activity and the antibody concentration, respectively. The symbols ♦, ■ and ▲ indicate the non-adsorbed fraction, the part of the adsorbed fraction and the anti-hIL-5Rα CDR-grafted antibody composition before separation, respectively.

ADCC activities of the non-adsorbed fraction and the part of the adsorbed fraction were measured by a method similar to the method described in Example 1(3). The non-adsorbed fraction had ADCC Activity higher than the anti-hIL-5Rα CDR-grafted antibody composition before separation, and the part of the adsorbed fraction showed ADCC activity lower than the anti-hIL-5Rα CDR-grafted antibody composition before separation (FIG. 9).

(4) Carbohydrate Analysis

Figure 10:
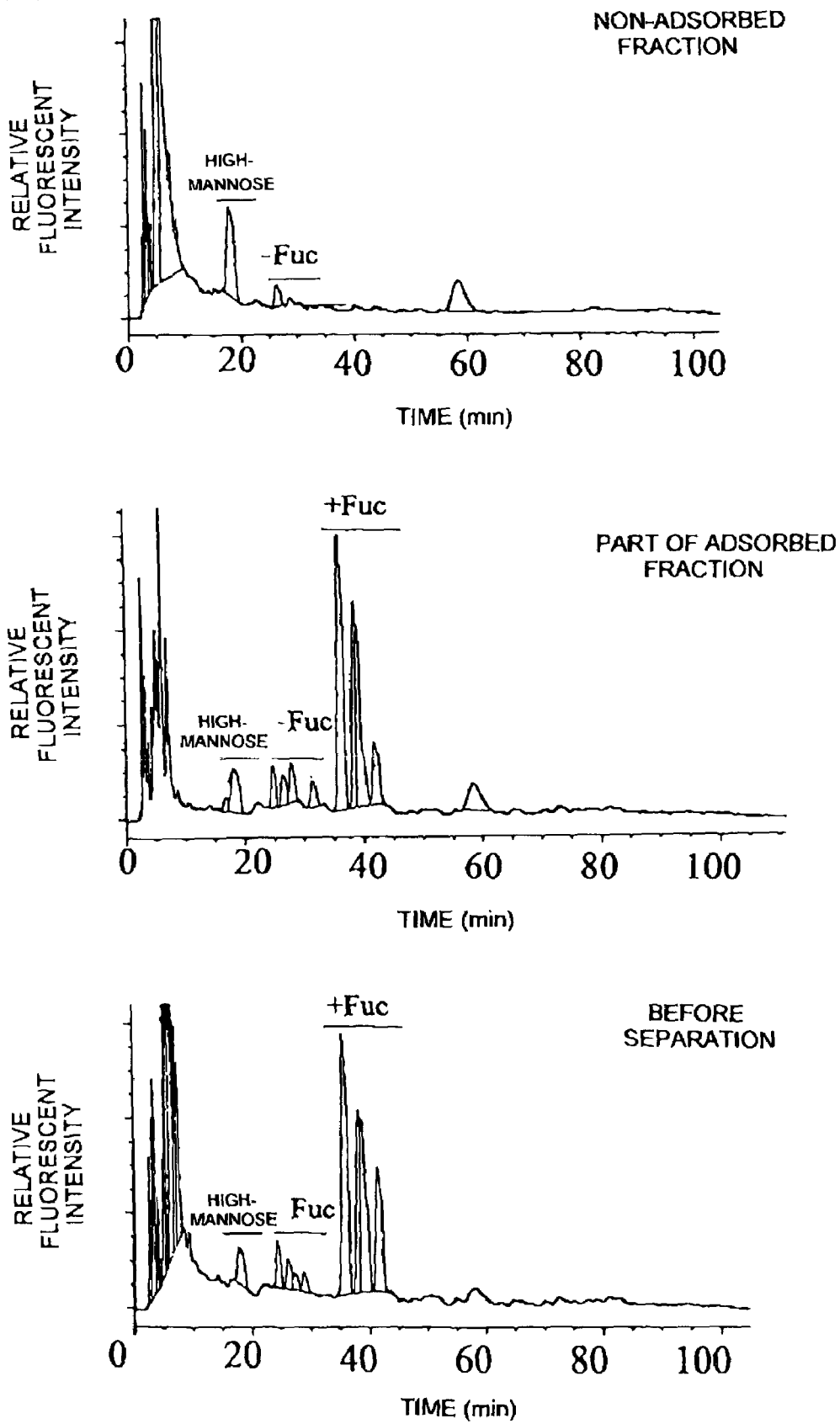
FIG. 10 is a drawing showing elution obtained by analyzing, with reverse phase HPLC, each of PA-labeled carbohydrates prepared from a non-adsorbed fraction or a part of an adsorbed fraction obtained by fractionating an anti-hIL-5Rα CDR-grafted antibody using a lectin binding to a carbohydrate having fucose and the anti-hIL-5Rα CDR-grafted antibody composition before separation. The upper figure, the middle figure, and the lower figure are drawings showing elutions of the non-adsorbed fraction, the part of the adsorbed fraction and the anti-hIL-5Rα CDR-grafted antibody composition before separation, respectively. The ordinate and the abscissa indicate the relative fluorescent intensity and the elution time, respectively. In the drawings, "−Fuc", "+Fuc" and "High-mannose" indicate carbonates having no fucose, carbonates having fucose and a high-mannose type carbohydrate, respectively.

Carbohydrates of the non-adsorbed fraction and the part of the adsorbed fraction were analyzed by the method described in Example 1(4) (FIG. 10). The PA-labeled carbohydrate group was eluted in the range of 15 minutes to 55 minutes. Based on the calculation from the peak areas, a high mannose-type carbohydrate and a complex-type carbohydrate having no fucose were 84% and 16%, respectively, in the non-adsorbed fraction. A high mannose-type carbohydrate and a complex-type carbohydrate having no fucose were 5% and 7%, respectively, in the part of the adsorbed fraction. A high mannose-type carbohydrate and a complex-type carbohydrate having no fucose were 7% and 8%, respectively, in the anti-hIL-5Rα CDR-grafted antibody composition before separation. Thus, an antibody composition containing a larger amount of carbohydrates having no fucose and an antibody composition containing a smaller amount of carbohydrates having no fucose than that contained in the anti-hIL-5Rα CDR-grafted antibody before separation can be separated each other and purified using a lectin column binding to a carbohydrate having fucose, regardless of a high mannose-type or complex-type carbohydrate.

EXAMPLE 6

Fractionation of an antibody composition comprising a large amount of a bisecting GlcNAc-bound carbohydrate:

(1) Fractionation of an Antibody Composition by Lectin Chromatography

An anti-hIL-5Rα CDR-grafted antibody composition was purified using a lectin binding to a carbohydrate having bisecting GlcNAc.

First, an expression vector for anti-hIL-5Rα CDR-grafted antibody produced according to the method described in WO97/10354 was introduced into a mouse myeloma NS0 cell to obtain a cell which produces the anti-hIL-5Rα CDR-grafted antibody. The cell was cultured in a culture medium and then the anti-hIL-5Rα CDR-grafted antibody composition was purified from the medium according to the method described in WO97/10354.

Next, a solution comprising the anti-hIL-5Rα CDR-grafted antibody purified in the above was passed through a lectin column (LA-PHA-$E_4$, 4.6×150 mm, manufactured by Honen Corporation). Using LC-6A manufactured by Shimadzu Corporation as an HPLC system, the solution was passed through the column at a flow rate of 0.5 ml/minute and at room temperature as the column temperature. The column was equilibrated with 50 mM tris-sulfate buffer (pH 8.0), and the purified anti-hIL-5Rα CDR-grafted antibody was injected and then eluted by a linear gradient (60 minutes) of 0 M to 0.2 M of $K_2B_4O_7$ (manufactured by Nacalai Tesque) in 50 mM tris-sulfate buffer (pH 8.0). The anti-hIL-5Rα CDR-grafted antibody composition was separated into an earlier eluted fraction (between 5 to 8 minutes) and a later eluted fraction (between 18 to 30 minutes).

(2) Carbohydrate Analysis

Figure 11:
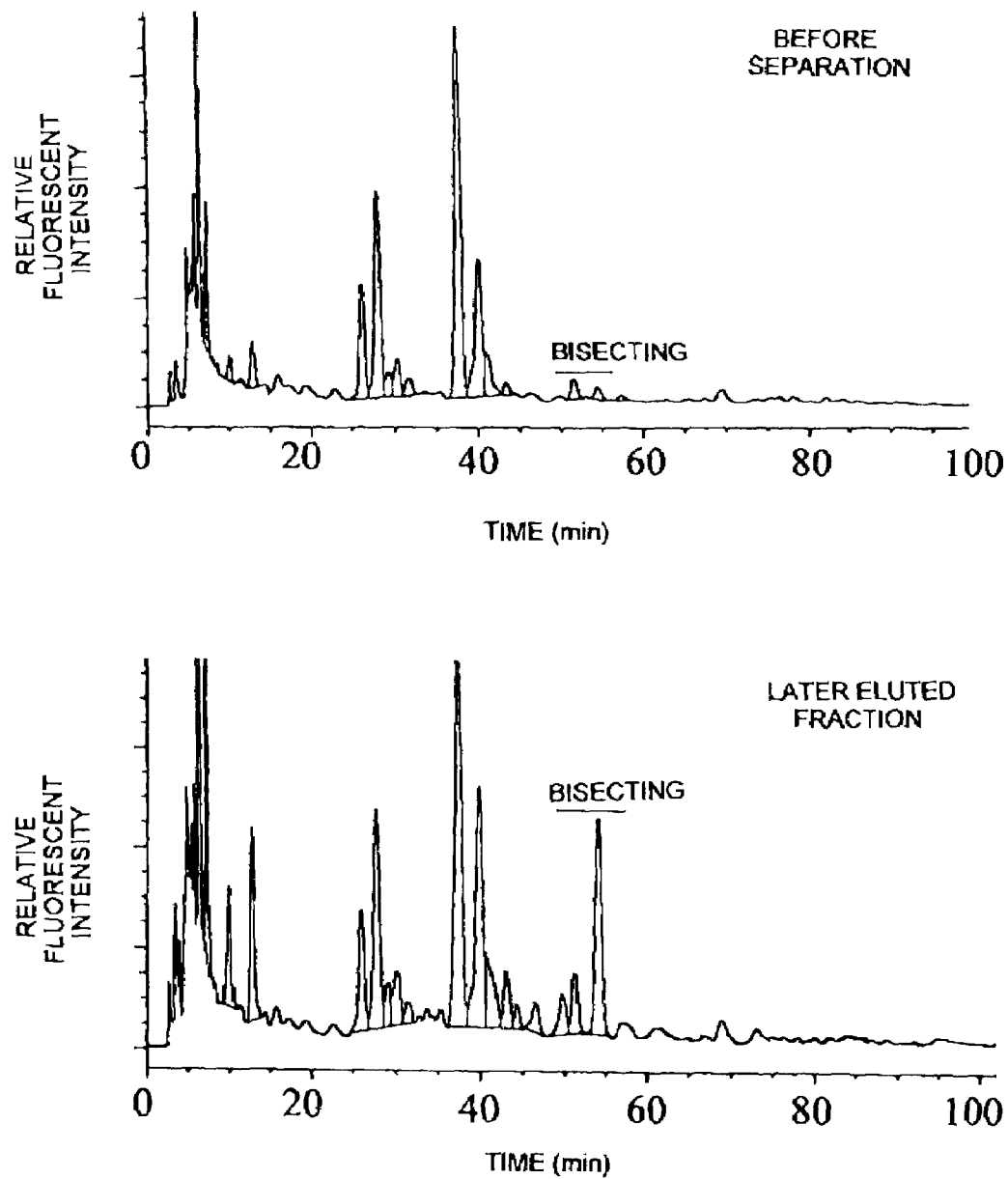
FIG. 11 is a drawing showing elution obtained by analyzing, with reverse phase HPLC, each of PA-labeled carbohydrates prepared from a later eluted fraction obtained by fractionating an anti-hIL-5Rα CDR-grafted antibody with chromatography using a PHA-$E_4$ lectin and the anti-hIL-5Rα CDR-grafted antibody composition before separation. The upper figure and the lower figure are drawings showing elutions of the anti-hIL-5Rα CDR-grafted antibody composition before separation and the later eluted fraction, respectively. The ordinate and the abscissa indicate the relative fluorescent intensity and the elution time, respectively. In the drawings, "bisecting" indicates carbonates to which bisecting GlcNAc is bound.

Carbohydrates in the later eluted fraction and the antibody composition before separation were analyzed by the method described in Example 1(4). The PA-labeled carbohydrate group was eluted in the range of 26 minutes to 55 minutes. As a result, the anti-hIL-5Rα CDR-grafted antibody composition of the later eluted fraction had a content of a carbohydrate having bisecting GlcNAc, increased from 4% to 21%, as compared with the anti-hIL-5Rα CDR-grafted antibody before purification and separation (FIG. 11).

EXAMPLE 7

Fractionation of an antibody composition comprising a small amount of a carbohydrate having fucose and a large amount of a bisecting GlcNAc-bound carbohydrate:

(1) Fractionation of Antibody Composition by Lectin Chromatography

The antibody composition comprising a large amount of a bisecting GlcNAc-bound carbohydrate obtained in Example 6(1) was separated into a non-adsorbed fraction and a part of an adsorbed fraction in a similar manner to the method described in Example 1(1).

(2) Carbohydrate Analysis

Figure 12:
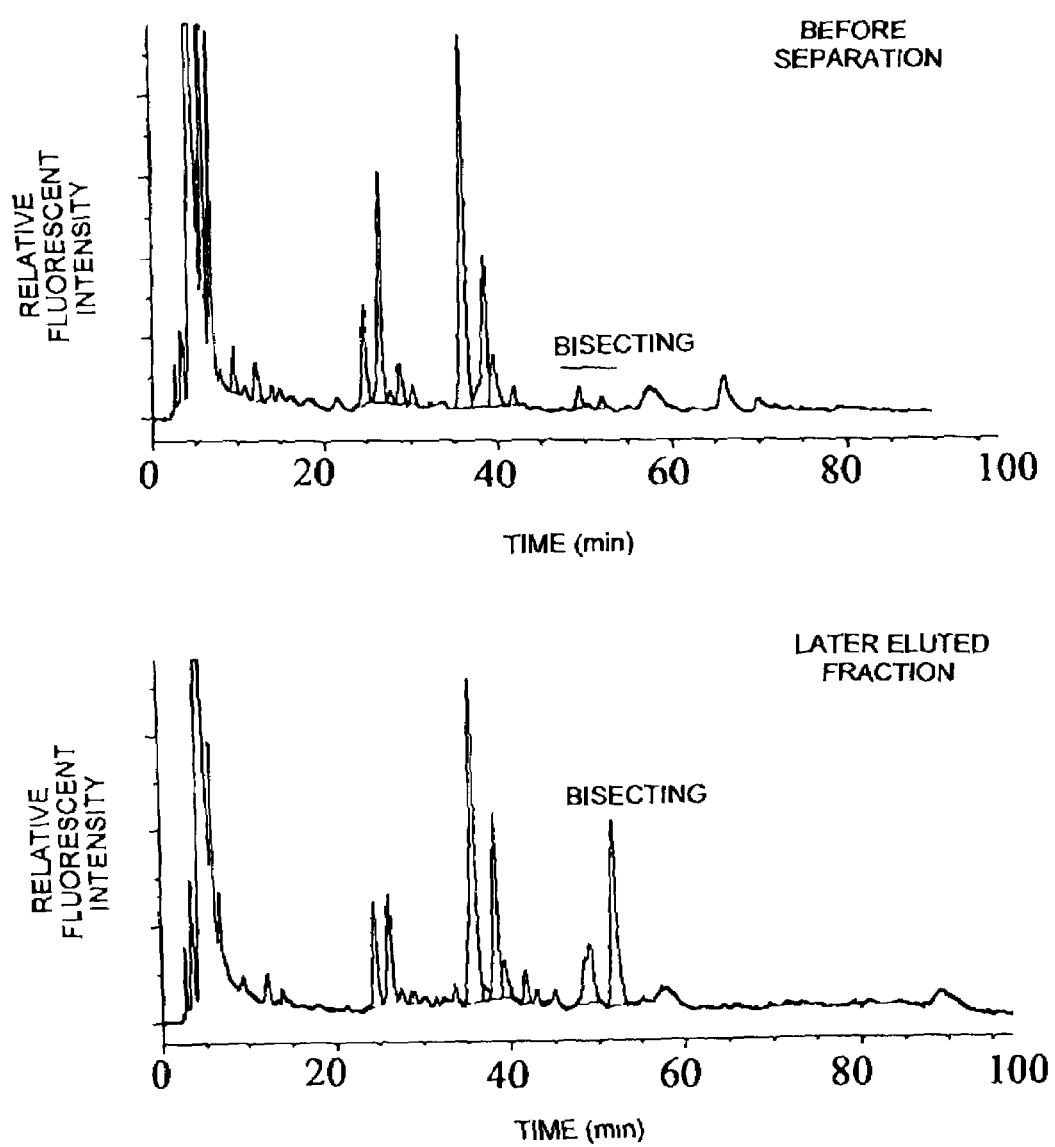
FIG. 12 is a drawing showing elution obtained by analyzing, with reverse phase HPLC, each of a PA-labeled carbohydrate prepared from the part of the adsorbed fraction of an anti-hIL-5Rα CDR-grafted antibody composition eluted from 18 minutes to 30 minutes with chromatography using a PHA-$E_4$ lectin and further fractionated using a LCA lectin and a PA-labeled carbohydrate prepared from the anti-hIL-5Rα CDR-grafted antibody composition before separation. The upper figure and the lower figure are drawings showing elutions of the anti-hIL-5Rα CDR-grafted antibody composition before separation and the fraction separated by two kinds of lectin chromatography, respectively. The ordinate and the abscissa indicate the relative fluorescent intensity and the elution time, respectively. In the drawings, "−Fuc" and "bisecting" indicates carbonates having no fucose and carbonates to which bisecting GlcNAc is bound, respectively.

Carbohydrates in the non-adsorbed fraction and the adsorbed fraction were analyzed by the method described in Example 1(4). The PA-labeled carbohydrates were eluted in the range of 25 minutes to 55 minutes. As a result, the part of the adsorbed fraction had a content of a carbohydrate having no fucose, decreased from 27% to 10%, and a content of a bisecting GlcNAc-bound carbohydrate, increased from 4% to 31%, as compared with the anti-hIL-5Rα CDR-grafted antibody composition before separation (FIG. 12).

While the invention has been described in detail and with reference to specific embodiments thereof, it will be apparent to one skill in the art that various changes and modifications can be made therein without departing from the spirit and scope thereof. All references cited herein are incorporated in their entirety.

What is claimed is:

1. A process for purifying an antibody composition having a desired property, which comprises:
    applying a solution containing the antibody composition to a column to which a lectin is immobilized to obtain a non-adsorbed fraction, said lectin being bound to a synthetic resin polymer; and
    recovering the antibody composition from the non-adsorbed fraction.

2. The process according to claim 1, wherein the lectin is at least one lectin selected from the group consisting of a concanavalin A, a wheat germ lectin, a *Lens culinaris* lectin and a *Phaseolus vulgaris* lectin $E_4$.

3. A process for purifying an antibody composition comprising an antibody having a carbohydrate structure to which bisecting N-acetylglucosamine is bound, which comprises:
    applying a solution containing the antibody composition to a column to which a wheat germ lectin or a *Phaseolus vulgaris* lectin $E_4$ is immobilized to adsorb the antibody composition to the column, said lectin being bound to a synthetic resin polymer;
    eluting the antibody composition from the column with an eluent to obtain an eluted fraction; and
    recovering the antibody composition from the eluted fraction.

4. A process for purifying an antibody composition having a higher antibody-dependent cell-mediated cytotoxic activity than the antibody composition before purification, which comprises:
    applying a solution containing the antibody composition to a column to which a wheat germ lectin or a *Phaseolus vulgaris* lectin $E_4$ is immobilized to adsorb the antibody composition to the column;
    eluting the antibody composition from the column with an eluent to obtain an eluted fraction; and
    recovering the antibody composition from the eluted fraction.

5. The process according to claim 4, wherein the lectin is immobilized to a synthetic resin polymer.

6. A process for purifying an antibody composition comprising an antibody having a carbohydrate structure to which fucose is not bound, which comprises:
    applying a solution containing the antibody composition to a column to which a *Lens culinaris* lectin is immobilized to obtain a non-adsorbed fraction, said lectin being bound to a synthetic resin polymer; and
    recovering the antibody composition from the non-adsorbed fraction.

7. A process for purifying an antibody composition having a higher antibody-dependent cell-mediated cytotoxic activity than the antibody composition before purification, which comprises:
    applying a solution containing the antibody composition to a column to which a *Lens culinaris* lectin is immobilized to obtain a non-adsorbed fraction; and
    recovering the antibody composition from the non-adsorbed fraction.

8. The process according to claim 7, wherein the lectin is immobilized to a synthetic resin polymer.

* * * * *